United States Patent
Wu et al.

(10) Patent No.: US 8,591,908 B2
(45) Date of Patent: Nov. 26, 2013

(54) IMMUNOGEN FOR PREPARATION OF THERAPEUTIC VACCINES OR DRUGS FOR TREATMENT OF HEPATITIS B AND THE PRODUCING METHOD AND USE THEREOF

(75) Inventors: Yuzhang Wu, Chongqing (CN); Jiang Bian, Chongqing (CN); Wei Zhou, Chongqing (CN); Zhengcai Jia, Chongqing (CN); Tongdong Shi, Chongqing (CN); Liyun Zou, Chongqing (CN)

(73) Assignees: Institute of Immunology, PLA, Chongqing (CN); Chongqing Jiachen Bioengineering Co., Ltd., Chongqing (CN)

( * ) Notice: Subject to any disclaimer, the term of this patent is extended or adjusted under 35 U.S.C. 154(b) by 852 days.

(21) Appl. No.: 10/528,350

(22) PCT Filed: Sep. 18, 2003

(86) PCT No.: PCT/CN03/00792
§ 371 (c)(1),
(2), (4) Date: Feb. 15, 2006

(87) PCT Pub. No.: WO2004/026899
PCT Pub. Date: Apr. 1, 2004

(65) Prior Publication Data
US 2006/0246089 A1 Nov. 2, 2006

(30) Foreign Application Priority Data
Sep. 18, 2002 (CN) .................................. 02 1 30738

(51) Int. Cl.
*A61K 39/00* (2006.01)
*A61K 39/29* (2006.01)
*A61K 9/127* (2006.01)
*C07K 14/02* (2006.01)

(52) U.S. Cl.
USPC .................. 424/189.1; 424/185.1; 424/227.1; 424/450; 530/350

(58) Field of Classification Search
None
See application file for complete search history.

(56) References Cited

U.S. PATENT DOCUMENTS 6,322,789 B1 * 11/2001 Vitiello et al. .............. 424/189.1
6,333,021 B1 * 12/2001 Schneider et al. .......... 424/9.52

OTHER PUBLICATIONS

K.H. Heermann, et al. "Large surface proteins of hepatitis B virus containing the pre-s sequence". J Virol. Nov. 1984; 52(2): 396-402.*
Madalinski K, et al. "Antibody responses to preS components after immunization of children with low doses of BioHepB." (Vaccine, 2001, 20(1-2):92-7).*
K.H. H Heermann, et al. "Large surface proteins of hepatitis B virus containing the pre-s sequence". J Virol. Nov. 1984; 52(2): 396-402.*
Roh S, "Induction of CTL responses and identification of a novel epitope of hepatitis B virus surface antigens in C57BL/6 mice immunized with recombinant vaccinia viruses" Virus Res. Jan. 2001;73(1):17-26.*
Tam JP et al. "Vaccine engineering: enhancement of immunogenicity of synthetic peptide vaccines related to hepatitis in chemically defined models consisting of T- and B-cell epitopes" PNAS 1989 86:9084-9088.*
Heathcote "A pilot study of the CU-1899 T-cell vaccine in subjects chronically infected with hepatitis B virus. The CY1899 T Cell Vaccine Study Group." (Hepatology. Aug. 1999;30(2):531-536).*
Chengalvala et al. "Enhanced immunogenicity of hepatitis B surface antigen by insertion of a helper T cell epitope from tetanus toxoid" Vaccine 17:1035-1041; 1999.*
Vitiello A. et al. Development of a Lipopeptide-based Therapeutic Vaccine to Treat Chronic HBV Infection J. Clin. Invest. 95:341-349; 1995.*
N.A. Mitchison: "T-cell-B-cell cooperation" Nature Reviews/immunology; 4:308-312, 2004.*
Immunology, 3rd Edition, Ivan Roitt • Jonathan Brostoff • David Male, 1993 by Mosby-Year Book Europe Limited. Total 6 pages provided.*
An, L.-L., and J.L. Whitton, "A Multivalent Minigene Vaccine, Containing B-Cell, Cytotoxic T-Lymphocyte, and $T_h$ Epitopes From Several Microbes, Induces Appropriate Responses In Vivo and Confers Protection Against More Than One Pathogen," *Journal of Virology* 71(3):2292-2302, Mar. 1997.
Shi, T.-D., et al., "Therapeutic Peptides Based on $HBcAg_{18-27}$ Epitope Can Induce CTL Response In Vitro and In Vivo," *Immunological Journal* 19(3):165-169, May 2003.
Wu, Y.Z., et al, "Studies on Molecular Design, Chemical Synthesis and Immunogenicity of Novel Antigenic Peptides Against Hepatitis B Virus," *ACTA Academiae Medicinae Militaris Tertiae* 22(10):919-923, Oct. 2000.

* cited by examiner

*Primary Examiner* — Shanon A Foley
(74) *Attorney, Agent, or Firm* — Christensen O'Connor Johnson Kindness PLLC

(57) ABSTRACT

The present invention relates to immunogens for treatment of hepatitis B and their preparation and use, and to vaccines or medicaments comprising said immunogens for treatment of hepatitis B and their preparation and use.

16 Claims, 9 Drawing Sheets

SEQUENCE LISTING

```
<160> NUMBER OF SEQ ID NOS: 74

<210> SEQ ID NO 1
<211> LENGTH: 44
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1

Xaa Ser Ser Gln Tyr Ile Lys Ala Asn Ser Lys Phe Ile Gly Ile Thr
1               5                   10                  15

Glu Ala Ala Ala Phe Leu Pro Ser Asp Phe Pro Ser Val Gly Gly
            20                  25                  30

Gly Asp Pro Arg Val Arg Gly Leu Tyr Phe Pro Ala
        35                  40

<210> SEQ ID NO 2
<211> LENGTH: 33
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: (CH3CH2CH=CHCH2CH=CH(CH2)CH=CH(CH2)7CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa Ser Ser Pro Ala Arg Glu Gly Gly Gly Trp Leu Ser Leu Leu Val
1               5                   10                  15

Pro Phe Val Ser Ser Ser Asp Pro Arg Val Arg Gly Leu Tyr Phe Pro
```

```
                    20                  25                  30

Ala

<210> SEQ ID NO 3
<211> LENGTH: 31
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CO, CH3CH2CH=CHCH2CH=CH(CH2)7CO7
<220> FEATURE:
<221> NAME/KEY: misc_feature
<222> LOCATION: (1)..(1)
<223> OTHER INFORMATION: Xaa can be any naturally occurring amino acid

<400> SEQUENCE: 3

Xaa Ser Ser Gln Tyr Ile Lys Ala Asn Ser Lys Phe Ile Gly Ile Thr
1               5                   10                  15

Glu Gly Gly Gly Asp Pro Arg Val Arg Gly Leu Tyr Phe Pro Ala
            20                  25                  30

<210> SEQ ID NO 4
<211> LENGTH: 43
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 4

Xaa Ser Ser Gln Tyr Ile Lys Ala Asn Ser Lys Phe Ile Gly Ile Thr
1               5                   10                  15

Glu Ala Ala Ala Phe Leu Pro Ser Asp Phe Phe Pro Ser Val Gly Gly
            20                  25                  30

Gly Cys Thr Lys Pro Thr Asp Gly Asn Cys Thr
            35                  40

<210> SEQ ID NO 5
<211> LENGTH: 44
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 5

Xaa Ser Ser Gln Tyr Ile Lys Ala Asn Ser Lys Phe Ile Gly Ile Thr
1               5                   10                  15

Glu Ala Ala Ala Ser Ile Val Ser Pro Phe Ile Pro Leu Leu Gly Gly
            20                  25                  30

Gly Asp Pro Arg Val Arg Gly Leu Tyr Phe Pro Ala
```

35  40

<210> SEQ ID NO 6
<211> LENGTH: 14
<212> TYPE: PRT
<213> ORGANISM: Unknown
<220> FEATURE:
<223> OTHER INFORMATION: Th cell epitope from tetanus toxoid or variant
      species thereof

<400> SEQUENCE: 6

Gln Tyr Ile Lys Ala Asn Ser Lys Phe Ile Gly Ile Thr Glu
1               5                   10

<210> SEQ ID NO 7
<211> LENGTH: 5
<212> TYPE: PRT
<213> ORGANISM: Unknown
<220> FEATURE:
<223> OTHER INFORMATION: Th cell epitope from tetanus toxoid or variant
      species thereof

<400> SEQUENCE: 7

Pro Ala Asp Arg Glu
1               5

<210> SEQ ID NO 8
<211> LENGTH: 8
<212> TYPE: PRT
<213> ORGANISM: Hepatitis B virus

<400> SEQUENCE: 8

Pro Leu Gly Phe Phe Pro Asp His
1               5

<210> SEQ ID NO 9
<211> LENGTH: 15
<212> TYPE: PRT
<213> ORGANISM: Hepatitis B virus

<400> SEQUENCE: 9

Met Gln Trp Asn Ser Thr Ala Leu His Gln Ala Leu Gln Asp Pro
1               5                   10                  15

<210> SEQ ID NO 10
<211> LENGTH: 10
<212> TYPE: PRT
<213> ORGANISM: Hepatitis B virus

<400> SEQUENCE: 10

Ser Ile Leu Ser Lys Thr Gly Asp Pro Val
1               5                   10

<210> SEQ ID NO 11
<211> LENGTH: 9
<212> TYPE: PRT
<213> ORGANISM: Hepatitis B virus

<400> SEQUENCE: 11

Val Leu Gln Ala Gly Phe Phe Leu Leu
1               5

<210> SEQ ID NO 12
<211> LENGTH: 9
<212> TYPE: PRT
<213> ORGANISM: Hepatitis B virus

```
<400> SEQUENCE: 12

Phe Leu Leu Thr Arg Ile Leu Thr Ile
1               5

<210> SEQ ID NO 13
<211> LENGTH: 9
<212> TYPE: PRT
<213> ORGANISM: Hepatitis B virus

<400> SEQUENCE: 13

Phe Leu Gly Gly Thr Pro Val Cys Leu
1               5

<210> SEQ ID NO 14
<211> LENGTH: 9
<212> TYPE: PRT
<213> ORGANISM: Hepatitis B virus

<400> SEQUENCE: 14

Leu Leu Cys Leu Ile Phe Leu Leu Val
1               5

<210> SEQ ID NO 15
<211> LENGTH: 10
<212> TYPE: PRT
<213> ORGANISM: Hepatitis B virus

<400> SEQUENCE: 15

Leu Leu Asp Tyr Gln Gly Met Leu Pro Val
1               5                   10

<210> SEQ ID NO 16
<211> LENGTH: 9
<212> TYPE: PRT
<213> ORGANISM: Hepatitis B virus

<400> SEQUENCE: 16

Trp Leu Ser Leu Leu Val Pro Phe Val
1               5

<210> SEQ ID NO 17
<211> LENGTH: 9
<212> TYPE: PRT
<213> ORGANISM: Hepatitis B virus

<400> SEQUENCE: 17

Gly Leu Tyr Ser Ser Thr Val Pro Val
1               5

<210> SEQ ID NO 18
<211> LENGTH: 10
<212> TYPE: PRT
<213> ORGANISM: Hepatitis B virus

<400> SEQUENCE: 18

Lys Val Leu His Lys Arg Thr Leu Gly Leu
1               5                   10

<210> SEQ ID NO 19
<211> LENGTH: 9
<212> TYPE: PRT
<213> ORGANISM: Hepatitis B virus

<400> SEQUENCE: 19

Val Leu His Lys Arg Thr Leu Gly Leu
```

```
<210> SEQ ID NO 20
<211> LENGTH: 10
<212> TYPE: PRT
<213> ORGANISM: Hepatitis B virus

<400> SEQUENCE: 20

Gly Leu Ser Ala Met Ser Thr Thr Asp Leu
1               5                   10

<210> SEQ ID NO 21
<211> LENGTH: 9
<212> TYPE: PRT
<213> ORGANISM: Hepatitis B virus

<400> SEQUENCE: 21

Cys Leu Phe Lys Asp Trp Glu Glu Leu
1               5

<210> SEQ ID NO 22
<211> LENGTH: 10
<212> TYPE: PRT
<213> ORGANISM: Hepatitis B virus

<400> SEQUENCE: 22

Val Leu Gly Gly Cys Arg His Lys Leu Val
1               5                   10

<210> SEQ ID NO 23
<211> LENGTH: 10
<212> TYPE: PRT
<213> ORGANISM: Hepatitis B virus

<400> SEQUENCE: 23

Phe Leu Pro Ser Asp Phe Phe Pro Ser Val
1               5                   10

<210> SEQ ID NO 24
<211> LENGTH: 11
<212> TYPE: PRT
<213> ORGANISM: Hepatitis B virus

<400> SEQUENCE: 24

Ser Thr Leu Pro Glu Thr Thr Val Val Arg Arg
1               5                   10

<210> SEQ ID NO 25
<211> LENGTH: 9
<212> TYPE: PRT
<213> ORGANISM: Hepatitis B virus

<400> SEQUENCE: 25

Glu Tyr Leu Val Ser Phe Gly Val Trp
1               5

<210> SEQ ID NO 26
<211> LENGTH: 9
<212> TYPE: PRT
<213> ORGANISM: Hepatitis B virus

<400> SEQUENCE: 26

Gly Leu Tyr Ser Ser Thr Val Pro Val
1               5
```

```
<210> SEQ ID NO 27
<211> LENGTH: 9
<212> TYPE: PRT
<213> ORGANISM: Hepatitis B virus

<400> SEQUENCE: 27

Gly Leu Ser Arg Tyr Val Ala Arg Leu
1               5

<210> SEQ ID NO 28
<211> LENGTH: 9
<212> TYPE: PRT
<213> ORGANISM: Hepatitis B virus

<400> SEQUENCE: 28

Phe Leu Leu Ser Leu Gly Ile His Leu
1               5

<210> SEQ ID NO 29
<211> LENGTH: 10
<212> TYPE: PRT
<213> ORGANISM: Hepatitis B virus

<400> SEQUENCE: 29

Ile Leu Arg Gly Thr Ser Phe Val Tyr Val
1               5                   10

<210> SEQ ID NO 30
<211> LENGTH: 9
<212> TYPE: PRT
<213> ORGANISM: Hepatitis B virus

<400> SEQUENCE: 30

Ser Leu Tyr Ala Asp Ser Pro Ser Val
1               5

<210> SEQ ID NO 31
<211> LENGTH: 9
<212> TYPE: PRT
<213> ORGANISM: Hepatitis B virus

<400> SEQUENCE: 31

Lys Tyr Thr Ser Phe Pro Trp Leu Leu
1               5

<210> SEQ ID NO 32
<211> LENGTH: 9
<212> TYPE: PRT
<213> ORGANISM: Hepatitis B virus

<400> SEQUENCE: 32

Ser Leu Tyr Ala Asp Ser Pro Ser Val
1               5

<210> SEQ ID NO 33
<211> LENGTH: 9
<212> TYPE: PRT
<213> ORGANISM: Hepatitis B virus

<400> SEQUENCE: 33

Ala Leu Met Pro Leu Tyr Ala Cys Ile
1               5

<210> SEQ ID NO 34
<211> LENGTH: 9
<212> TYPE: PRT
```

<213> ORGANISM: Hepatitis B virus

<400> SEQUENCE: 34

Tyr Met Asp Asp Val Val Leu Gly Ala
1               5

<210> SEQ ID NO 35
<211> LENGTH: 9
<212> TYPE: PRT
<213> ORGANISM: Hepatitis B virus

<400> SEQUENCE: 35

Trp Ile Leu Arg Gly Thr Ser Phe Val
1               5

<210> SEQ ID NO 36
<211> LENGTH: 9
<212> TYPE: PRT
<213> ORGANISM: Hepatitis B virus

<400> SEQUENCE: 36

Lys Leu His Leu Tyr Ser His Pro Ile
1               5

<210> SEQ ID NO 37
<211> LENGTH: 9
<212> TYPE: PRT
<213> ORGANISM: Hepatitis B virus

<400> SEQUENCE: 37

Phe Thr Gln Ala Gly Tyr Pro Ala Leu
1               5

<210> SEQ ID NO 38
<211> LENGTH: 10
<212> TYPE: PRT
<213> ORGANISM: Hepatitis B virus

<400> SEQUENCE: 38

Ser Leu Asn Phe Leu Gly Gly Thr Thr Val
1               5                   10

<210> SEQ ID NO 39
<211> LENGTH: 10
<212> TYPE: PRT
<213> ORGANISM: Hepatitis B virus

<400> SEQUENCE: 39

Leu Leu Asp Tyr Gln Gly Met Leu Pro Val
1               5                   10

<210> SEQ ID NO 40
<211> LENGTH: 10
<212> TYPE: PRT
<213> ORGANISM: Hepatitis B virus

<400> SEQUENCE: 40

Leu Leu Val Pro Phe Val Gln Trp Phe Val
1               5                   10

<210> SEQ ID NO 41
<211> LENGTH: 10
<212> TYPE: PRT
<213> ORGANISM: Hepatitis B virus

<400> SEQUENCE: 41

```
Gly Leu Ser Pro Thr Val Trp Leu Ser Val
1               5                   10

<210> SEQ ID NO 42
<211> LENGTH: 10
<212> TYPE: PRT
<213> ORGANISM: Hepatitis B virus

<400> SEQUENCE: 42

Leu Leu Pro Ile Phe Phe Cys Leu Trp Val
1               5                   10

<210> SEQ ID NO 43
<211> LENGTH: 7
<212> TYPE: PRT
<213> ORGANISM: Hepatitis B virus

<400> SEQUENCE: 43

Tyr Val Asn Thr Asn Met Gly
1               5

<210> SEQ ID NO 44
<211> LENGTH: 12
<212> TYPE: PRT
<213> ORGANISM: Hepatitis B virus

<400> SEQUENCE: 44

Tyr Val Asn Thr Asn Met Gly Leu Lys Ser Glu Gln
1               5                   10

<210> SEQ ID NO 45
<211> LENGTH: 10
<212> TYPE: PRT
<213> ORGANISM: Hepatitis B virus

<400> SEQUENCE: 45

Ser Ile Leu Ser Lys Thr Gly Asp Pro Val
1               5                   10

<210> SEQ ID NO 46
<211> LENGTH: 10
<212> TYPE: PRT
<213> ORGANISM: Hepatitis B virus

<400> SEQUENCE: 46

Gly Leu Ser Pro Thr Val Trp Leu Ser Val
1               5                   10

<210> SEQ ID NO 47
<211> LENGTH: 10
<212> TYPE: PRT
<213> ORGANISM: Hepatitis B virus

<400> SEQUENCE: 47

Ser Ile Val Ser Pro Phe Ile Pro Leu Leu
1               5                   10

<210> SEQ ID NO 48
<211> LENGTH: 11
<212> TYPE: PRT
<213> ORGANISM: Hepatitis B virus

<400> SEQUENCE: 48

Asp Pro Arg Val Arg Gly Leu Tyr Phe Pro Ala
1               5                   10
```

```
<210> SEQ ID NO 49
<211> LENGTH: 10
<212> TYPE: PRT
<213> ORGANISM: Hepatitis B virus

<400> SEQUENCE: 49

Cys Thr Lys Pro Thr Asp Gly Asn Cys Thr
1               5                   10

<210> SEQ ID NO 50
<211> LENGTH: 35
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)10CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 50

Xaa Ser Ser Pro Ala Asp Arg Glu Gly Gly Ser Leu Asn Phe Leu
1               5                   10                  15

Gly Gly Thr Thr Val Ser Ser Ser Asp Pro Arg Val Arg Gly Leu Tyr
            20                  25                  30

Phe Pro Ala
        35

<210> SEQ ID NO 51
<211> LENGTH: 43
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 51

Xaa Ser Ser Gln Tyr Ile Lys Ala Asn Ser Lys Phe Ile Gly Ile Thr
1               5                   10                  15

Glu Ala Ala Ala Leu Leu Cys Leu Ile Phe Leu Leu Val Gly Gly Gly
            20                  25                  30

Asp Pro Arg Val Arg Gly Leu Tyr Phe Pro Ala
        35                  40

<210> SEQ ID NO 52
<211> LENGTH: 35
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)16CO
<220> FEATURE:
<221> NAME/KEY: misc_feature
<222> LOCATION: (1)..(1)
```

-continued

<223> OTHER INFORMATION: Xaa can be any naturally occurring amino acid

<400> SEQUENCE: 52

Xaa Ser Ser Pro Ala Asp Arg Glu Ala Ala Ala Leu Leu Asp Tyr Gln
1               5                   10                  15

Gly Met Leu Pro Val Gly Gly Gly Asp Pro Arg Val Arg Gly Leu Tyr
            20                  25                  30

Phe Pro Ala
        35

<210> SEQ ID NO 53
<211> LENGTH: 20
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)7CH=CH(CH2)-CO, CH3
      CH2CH=CHCH2CH=CH(CH2)7CO7
<220> FEATURE:
<221> NAME/KEY: misc_feature
<222> LOCATION: (1)..(1)
<223> OTHER INFORMATION: Xaa can be any naturally occurring amino acid

<400> SEQUENCE: 53

Xaa Ser Ser Gln Tyr Ile Lys Ala Asn Ser Lys Phe Ile Gly Ile Thr
1               5                   10                  15

Glu Gly Gly Gly
            20

<210> SEQ ID NO 54
<211> LENGTH: 24
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Phe with the following N-terminal
      modification: CH3CH2CH=CHCH2CH=CH(CH2)CH=CH(CH2)7CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 54

Xaa Leu Pro Ser Asp Phe Phe Pro Ser Val Ala Ala Ala Asp Pro Arg
1               5                   10                  15

Val Arg Gly Leu Tyr Phe Pro Ala
            20

<210> SEQ ID NO 55
<211> LENGTH: 34
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3CH2CH=CHCH2CH=CH(CH2)CH=CH(CH2)7CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 55

```
Xaa Ser Ser Pro Ala Asp Arg Glu Gly Gly Gly Trp Leu Ser Leu Leu
1               5                   10                  15

Val Pro Phe Val Ser Ser Asp Pro Arg Val Arg Gly Leu Tyr Phe
            20                  25                  30

Pro Ala

<210> SEQ ID NO 56
<211> LENGTH: 35
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 56

Xaa Ser Ser Pro Ala Asp Arg Glu Ala Ala Ala Phe Leu Pro Ser Asp
1               5                   10                  15

Phe Phe Pro Ser Val Gly Gly Asp Pro Arg Val Arg Gly Leu Tyr
            20                  25                  30

Phe Pro Ala
        35

<210> SEQ ID NO 57
<211> LENGTH: 35
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 57

Xaa Ser Ser Pro Ala Asp Arg Glu Gly Gly Gly Leu Leu Val Pro Phe
1               5                   10                  15

Val Gln Trp Phe Val Ser Ser Asp Pro Arg Val Arg Gly Leu Tyr
            20                  25                  30

Phe Pro Ala
        35

<210> SEQ ID NO 58
<211> LENGTH: 35
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 58
```

```
Xaa Ser Ser Pro Ala Asp Arg Glu Ala Ala Gly Leu Ser Pro Thr
1               5                   10                  15

Val Trp Leu Ser Val Gly Gly Gly Asp Pro Arg Val Arg Gly Leu Tyr
                20                  25                  30

Phe Pro Ala
            35

<210> SEQ ID NO 59
<211> LENGTH: 35
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)16CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 59

Xaa Ser Ser Pro Ala Asp Arg Glu Ala Ala Leu Leu Pro Ile Phe
1               5                   10                  15

Phe Cys Leu Trp Val Gly Gly Gly Asp Pro Arg Val Arg Gly Leu Tyr
                20                  25                  30

Phe Pro Ala
            35

<210> SEQ ID NO 60
<211> LENGTH: 41
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)16CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 60

Xaa Ser Ser Gln Tyr Ile Lys Ala Asn Ser Lys Phe Ile Gly Ile Thr
1               5                   10                  15

Glu Ala Ala Ala Tyr Val Asn Thr Asn Met Gly Gly Gly Gly Asp Pro
                20                  25                  30

Arg Val Arg Gly Leu Tyr Phe Pro Ala
            35                  40

<210> SEQ ID NO 61
<211> LENGTH: 44
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 61
```

```
Xaa Ser Ser Gln Tyr Ile Lys Ala Asn Ser Lys Phe Ile Gly Ile Thr
1               5                   10                  15

Glu Gly Gly Gly Phe Leu Pro Ser Asp Phe Pro Ser Val Ser Ser
            20                  25                  30

Ser Asp Pro Arg Val Arg Gly Leu Tyr Phe Pro Ala
        35                  40

<210> SEQ ID NO 62
<211> LENGTH: 43
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 62

Xaa Ser Ser Gln Tyr Ile Lys Ala Asn Ser Lys Phe Ile Gly Ile Thr
1               5                   10                  15

Glu Ala Ala Ala Tyr Val Asn Thr Asn Met Gly Leu Lys Gly Gly Gly
            20                  25                  30

Asp Pro Arg Val Arg Gly Leu Tyr Phe Pro Ala
        35                  40

<210> SEQ ID NO 63
<211> LENGTH: 42
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 63

Xaa Ser Ser Gln Tyr Ile Lys Ala Asn Ser Lys Phe Ile Gly Ile Thr
1               5                   10                  15

Glu Ala Ala Ala Pro Leu Gly Phe Phe Pro Asp His Gly Gly Gly Asp
            20                  25                  30

Pro Arg Val Arg Gly Leu Tyr Phe Pro Ala
        35                  40

<210> SEQ ID NO 64
<211> LENGTH: 49
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid
```

-continued

```
<400> SEQUENCE: 64

Xaa Ser Ser Gln Tyr Ile Lys Ala Asn Ser Lys Phe Ile Gly Ile Thr
1               5                   10                  15

Glu Ala Ala Ala Met Gln Trp Asn Ser Thr Ala Leu His Gln Ala Leu
            20                  25                  30

Gln Asp Pro Gly Gly Gly Asp Pro Arg Val Arg Gly Leu Tyr Phe Pro
        35                  40                  45

Ala

<210> SEQ ID NO 65
<211> LENGTH: 35
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 65

Xaa Ser Ser Pro Asp Ala Arg Glu Ala Ala Ser Ile Leu Ser Lys
1               5                   10                  15

Thr Gly Asp Pro Val Gly Gly Gly Asp Pro Arg Val Arg Gly Leu Tyr
            20                  25                  30

Phe Pro Ala
        35

<210> SEQ ID NO 66
<211> LENGTH: 34
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)16CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 66

Xaa Ser Ser Pro Ala Asp Arg Glu Ala Ala Val Leu Gln Ala Gly
1               5                   10                  15

Phe Phe Leu Leu Gly Gly Gly Asp Pro Arg Val Arg Gly Leu Tyr Phe
            20                  25                  30

Pro Ala

<210> SEQ ID NO 67
<211> LENGTH: 34
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)16CO
<220> FEATURE:
<221> NAME/KEY: misc_feature
<222> LOCATION: (1)..(1)
```

-continued

<223> OTHER INFORMATION: Xaa can be any naturally occurring amino acid

<400> SEQUENCE: 67

Xaa Ser Ser Pro Ala Asp Arg Glu Ser Ser Ser Phe Leu Leu Thr Arg
1               5                   10                  15

Ile Leu Thr Ile Gly Gly Gly Asp Pro Arg Val Arg Gly Leu Tyr Phe
            20                  25                  30

Pro Ala

<210> SEQ ID NO 68
<211> LENGTH: 34
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)16CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 68

Xaa Ser Ser Pro Ala Asp Arg Glu Ala Ala Ala Phe Leu Gly Gly Thr
1               5                   10                  15

Pro Val Cys Leu Gly Gly Gly Asp Pro Arg Val Arg Gly Leu Tyr Phe
            20                  25                  30

Pro Ala

<210> SEQ ID NO 69
<211> LENGTH: 44
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 69

Xaa Ser Ser Gln Tyr Ile Lys Ala Asn Ser Lys Phe Ile Gly Ile Thr
1               5                   10                  15

Glu Ala Ala Ala Gly Leu Ser Pro Thr Val Trp Leu Ser Val Gly Gly
            20                  25                  30

Gly Asp Pro Arg Val Arg Gly Leu Tyr Phe Pro Ala
        35                  40

<210> SEQ ID NO 70
<211> LENGTH: 36
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)16CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 70

Xaa Ser Ser Pro Ala Asp Arg Glu Ala Ala Ala Ser Thr Leu Pro Glu
1               5                   10                  15

Thr Thr Val Val Arg Arg Gly Gly Gly Asp Pro Arg Val Arg Gly Leu
            20                  25                  30

Tyr Phe Pro Ala
        35

<210> SEQ ID NO 71
<211> LENGTH: 41
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3CH2CH=CHCH2CH=CH(CH2)CH=CH(CH2)7CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 71

Xaa Ser Ser Pro Ala Asp Arg Glu Gly Gly Gly Trp Leu Ser Leu Leu
1               5                   10                  15

Val Pro Phe Val Ser Ser Ser Asp Pro Arg Val Arg Gly Leu Tyr Phe
            20                  25                  30

Pro Ala Arg Gly Leu Tyr Phe Pro Ala
        35                  40

<210> SEQ ID NO 72
<211> LENGTH: 48
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)14CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 72

Xaa Ser Ser Tyr Ile Lys Ala Asn Ser Lys Phe Ile Gly Ile Thr Glu
1               5                   10                  15

Ala Ala Ala Met Gln Trp Asn Ser Thr Ala Leu His Gln Ala Leu Gln
            20                  25                  30

Asp Pro Gly Gly Gly Asp Pro Arg Val Arg Gly Leu Tyr Phe Pro Ala
        35                  40                  45

<210> SEQ ID NO 73
<211> LENGTH: 28
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)7CH=CH(CH2)CO,
      CH3CH2CH=CHCH2CH=CH(CH2)7CO7
<220> FEATURE:
<221> NAME/KEY: misc_feature -continued

```
<222> LOCATION: (1)..(1)
<223> OTHER INFORMATION: Xaa can be any naturally occurring amino acid

<400> SEQUENCE: 73

Xaa Ser Ser Gln Tyr Ile Lys Ala Asn Ser Lys Phe Ile Gly Ile Thr
1               5                   10                  15

Glu Gly Gly Gly Asp Pro Arg Val Arg Gly Leu Tyr
            20                  25

<210> SEQ ID NO 74
<211> LENGTH: 44
<212> TYPE: PRT
<213> ORGANISM: Artificial Sequence
<220> FEATURE:
<223> OTHER INFORMATION: Immunogen
<220> FEATURE:
<221> NAME/KEY: MISC_FEATURE
<223> OTHER INFORMATION: Xaa is Lys with the following N-terminal
      modification: CH3(CH2)16CO
<220> FEATURE:
<221> NAME/KEY: misc_feature
<222> LOCATION: (1)..(1)
<223> OTHER INFORMATION: Xaa can be any naturally occurring amino acid

<400> SEQUENCE: 74

Xaa Ser Ser Gln Tyr Ile Lys Ala Asn Ser Lys Phe Ile Gly Ile Thr
1               5                   10                  15

Glu Ala Ala Ala Phe Leu Pro Ser Asp Phe Phe Pro Ser Val Gly Gly
            20                  25                  30

Gly Asp Pro Arg Val Arg Gly Leu Tyr Phe Pro Ala
        35                  40
```

IMMUNOGEN FOR PREPARATION OF THERAPEUTIC VACCINES OR DRUGS FOR TREATMENT OF HEPATITIS B AND THE PRODUCING METHOD AND USE THEREOF

TECHNICAL FIELD

The present invention relates to immunogens for treatment of hepatitis B and their preparation and use; and to vaccines or medicaments comprising said immunogens for treatment of hepatitis B and their preparation and use.

BACKGROUND ART

Hepatitis B is one of global diseases. According to the WHO's report, about 30% of the population in the world, i.e., 1.8 billion, are infected by hepatitis B virus, among them about 350 millions are chronically infected. The latter exhibit a continuous viremia, and the virus level is 100-1000 times higher than that of AIDS virus (HIV) or hepatitis C virus (HCV). China is one of the high-risk regions in the world, with carriers of hepatitis B virus being about 10% of the total population, i.e., about 120 millions, and patients of chronic hepatitis being about 30 millions. Most cases of hepatitis B were infected during perinatal period, developed during adolescence, and exacerbated in young adults. Thus, it mainly endangers young adults. Most patients are spontaneously cured after infection, while some patients are not cured, and liver cirrhosis and liver cancer are developed. It is estimated that at least 500 thousands patients of chronic hepatitis die of liver cirrhosis and liver cancer. Hepatitis B virus (HBV) is a human carcinogen only next to tobacco.

At present, the main means for controlling prevalence of hepatitis B is the global immunization program practiced by WHO. However, because of (1) the program employs preventive vaccine, which is ineffective to infected persons; (2) 5-15% uninfected neonates do not respond to said vaccine; and (3) the inoculation rate is low, and according to the statistics in 1999, the inoculation rate of neonates in high-risk regions in the world is only 62%. Thus, during a relatively long period in future, hepatitis B will still be one of the most serious diseases harmful to people's health.

The positive rates of HBV core antigen (HBcAg) in hepatic carcinoma and paraneoplastic tissues are 62.5% and 29.2% respectively. At present, it has been proven that: (1) as a hepatotropic virus, HBV cannot directly cause damage of liver cells, rather, the pathology and clinical results of HBV infection depend on immunologic mechanism; and (2) as an intracellular infection, the chronic persistent infection state is mainly associated with the relatively weakness of the cellular immune response in vivo, wherein HBV-specific cytotoxic T lymphocyte (CTL) response determines the final result of HBV infection. If a patient has a high level of CTL activity after HBV infection, viruses will be eliminated in vivo and the patient will recover; while if a patient has a low or undetectable level of CTL activity after HBV infection, the patient will be in a chronic persistent infection state, and a liver cirrhosis or liver cancer will be further developed. Thus, the chronic HBV persistent infection state could be treated and the relevant secondary liver cirrhosis and liver cancer could be prevented by overcoming the immune tolerance in patients with HBV persistent infection and initiating the HBV specific CTL response in vivo.

F. V. Chisari in Scripps Institute (U.S.) filed four patent applications (U.S. Pat. No. 6,235,288, U.S. Pat. No. 5,932,224, U.S. Pat. No. 5,840,303, and U.S. Pat. No. 5,788,969) based on his own studies. These patent applications all relate to CTL epitopes determined on HBV antigens. These epitopes are separately from core antigens, surface antigens, polymerases, and X antigens. These parts or structures are recognizable by CTL induced by HBV. Jiangxi Nanchang Medical College (China) filed an application, seeking to protect a plasmid DNA vaccine comprising Pre-S2 and HBsAg, which stimulates cellular immunity and humoral immunity and is useful for the prevention and treatment of hepatitis B.

At present, there is no specific therapeutic method for treatment of chronic HBV persistent infection state (including virus carrier, chronic persistent hepatitis, and chronic active hepatitis). Interferons (IFN-$\alpha/\beta$, IFN-$\gamma$) and tumor necrosis factors (TNF-$\alpha$) are proven to be able to down regulate the replication and gene expression of HBV in infected cells, and are sensitive to replicating DNA intermediates and transcription template, but they cannot eliminate virus. Lamivudine (3TC) is the first nucleoside medicament in clinical use for inhibiting virus replication, which is able to reduce viremia for up to 2 times log, but can hardly eliminate virus, because the virus titer in E antigen positive carriers is more than $10^8$. In fact, no treated patient has been found to become HBsAg negative. Hence, it is badly in need to develop an effective means for treating chronic HBV persistent infection state.

SUMMARY OF THE INVENTION

The first object of the present invention is to provide an immunogen capable of inducing HBV-specific CTL and a therapeutic vaccine comprising said immunogen.

The second object of the present invention is to provide a method for preparing said immunogen and a method for preparing said vaccine for treatment of hepatitis B.

The third object of the present invention is to provide use of said immunogen in manufacture of a vaccine or a medicament for treatment of hepatitis B.

The present invention also provides use of said immunogen in manufacture of a vaccine or a medicament for treatment of the chronic HBV persistent infection state and the relevant secondary diseases such as liver cirrhosis, liver cancer, etc.

Figure 1:
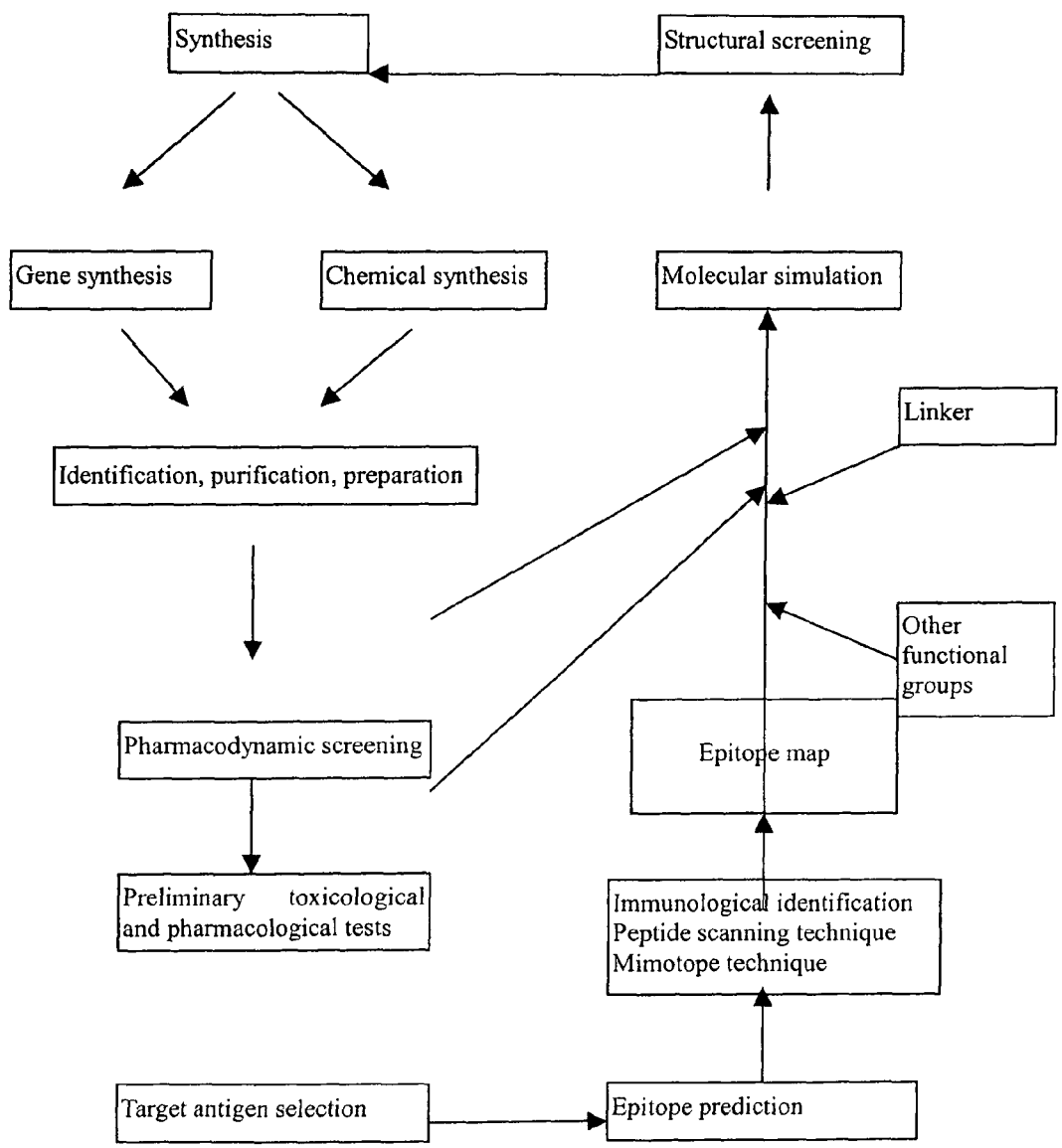
FIG. 1 is a schematic diagram of an epitope-based vaccine design (EBVD). Firstly, a target antigen is selected, and its epitope map is obtained by a high resolution immunological recognition study. Based on said epitope map, an immunogen is designed by molecular design and molecular simulation techniques. The immunogen molecule is prepared via chemical or genetic synthesis, functionally screened and preliminarily evaluated in terms of toxicology and pharmacokinetics. After analysis of structure-activity relation, the molecule is modified and optimized, and then is synthesized and further evaluated in the next cycle. After about 200 cycles, a leader structure may be obtained.
Figure 2:
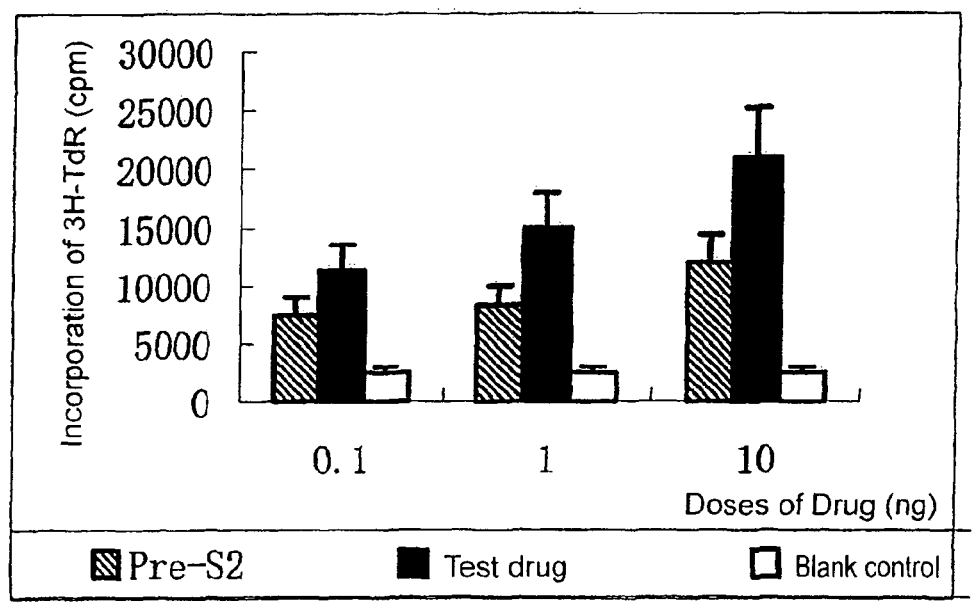
FIG. 2 indicated the effect of inducing the proliferation of lymphocytes. Peripheral blood mononuclear lymphocytes were isolated from fresh peripheral blood of HLA-A2+ healthy person by the Ficoll-Hypaque method, and were cultured in vitro in RPMI1640 culture media (containing 10% fetal calf serum) on a 96-well cell culture plate ($10^6$ cells per well). IL-2 (5 IU) and the test drug were separately added into the test drug group ($CH_3(CH_2)_{14}$COKSSQYIKANSKFIG-ITEAAAFLPSDFFPSVGGGDPRVRGLYFPA) (SEQ ID NO:1), the Pre-S2 control group and the blank control group; these cells were further cultured for six days and were stimulated with IL-2 and the test drug at the same doses for 48 hours; then ³H-TdR (1 μCi/ml) was added, and the cells were further cultured for 18 hours before they were harvested and the γ-count values were measured. The results indicated that the test drug could significantly induce the proliferation of lymphocytes, the minimal effective dose was 0.1 ng, and a dose-effect dependence was observed in the range of 0.1-10 ng.
Figure 3A:
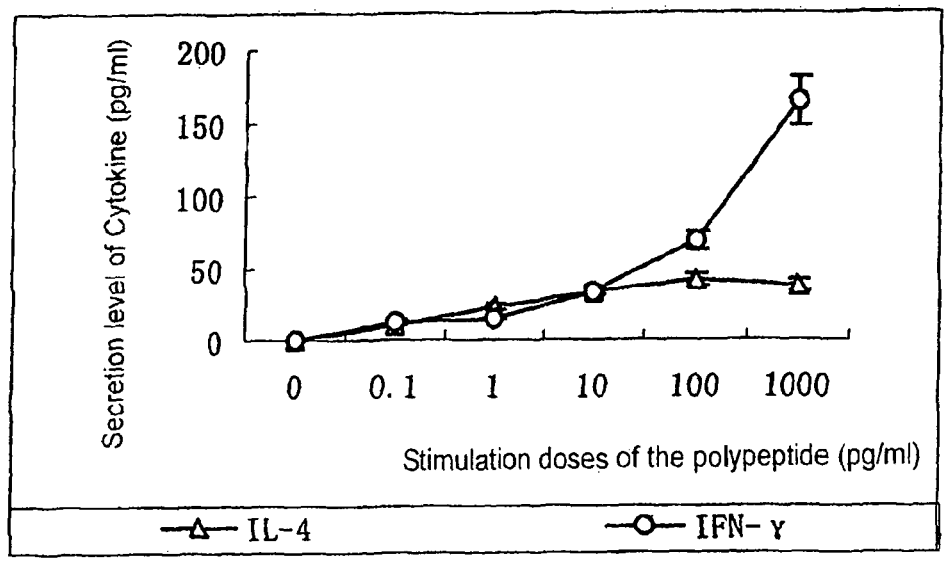
Figure 3B:
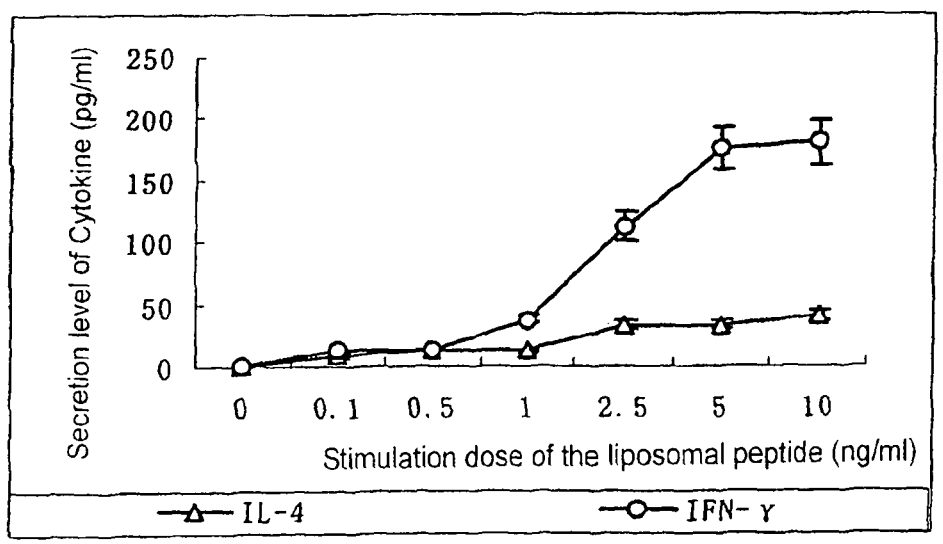

FIG. 3 indicated the effect of inducing Th1 activation. Peripheral blood mononuclear lymphocytes were isolated from fresh peripheral blood of HLA-A2+ healthy person by the Ficoll-Hypaque method, and were cultured in vitro in RPMI1640 culture media (containing 10% fetal calf serum and 100 U/ml penicillin-streptomycin) on a 24-well cell culture plate ($10^6$ cells per well) in groups. IL-2 (301 U) and the test drugs ($CH_3CH_2CH=CHCH_2CH=CH(CH_2)CH=CH(CH_2)_7COKSSPAREGGGWLSLLVPFVSSSDP$ RVRGLYFPA) (SEQ ID NO:2) (at different doses) were separately added, and the cells were further cultured for six days. Then the cells were stimulated with IL-2 and the test drug at the same doses once a week for three times. Twenty-four hours after the last stimulation, the levels of IL-4 and IFN-γ in the culture supernatant were measured by the ELISA method. The results indicated that the test drug could induce the secretion of IFN-γ in a notable dose-effect dependence relation, while the effect of inducing the secretion of IL-4 is not obvious, suggesting that the test drug strongly induced the activation of Th1 type T cells, yet induced the activation of Th2 type T cells weakly.

Figure 4A:
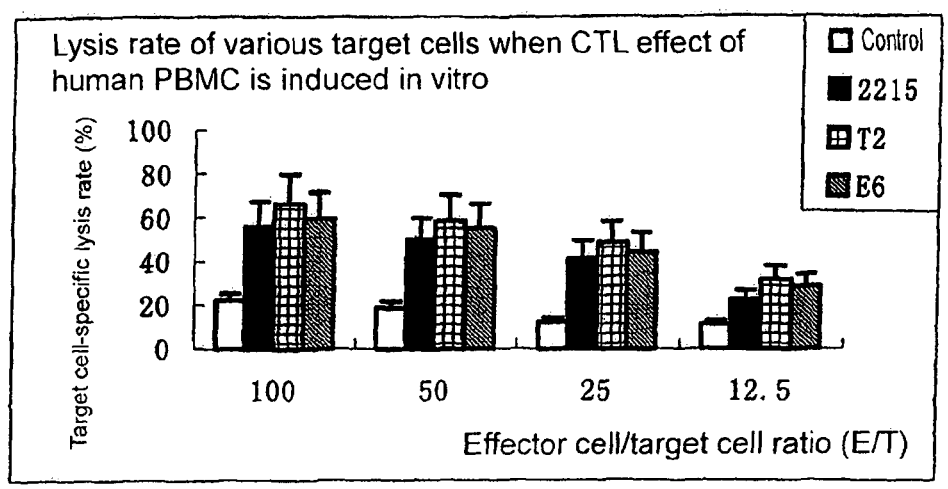
Figure 4B:
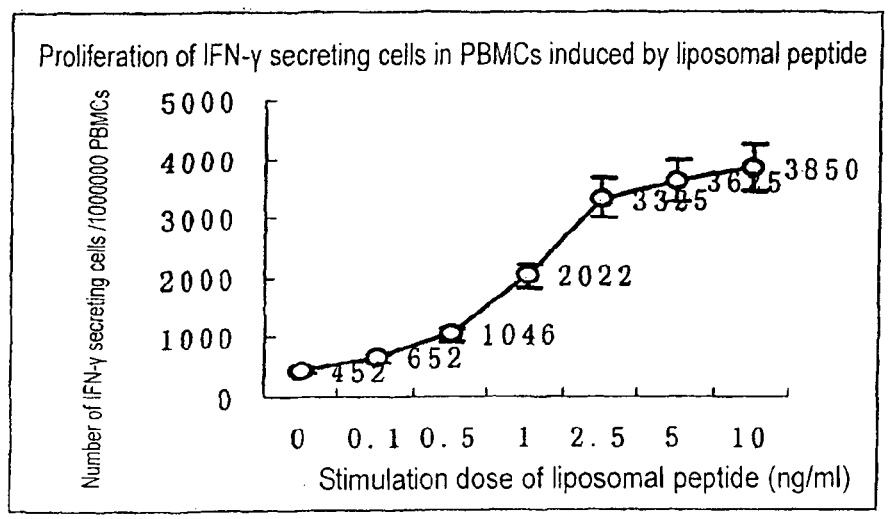
Figure 4C:
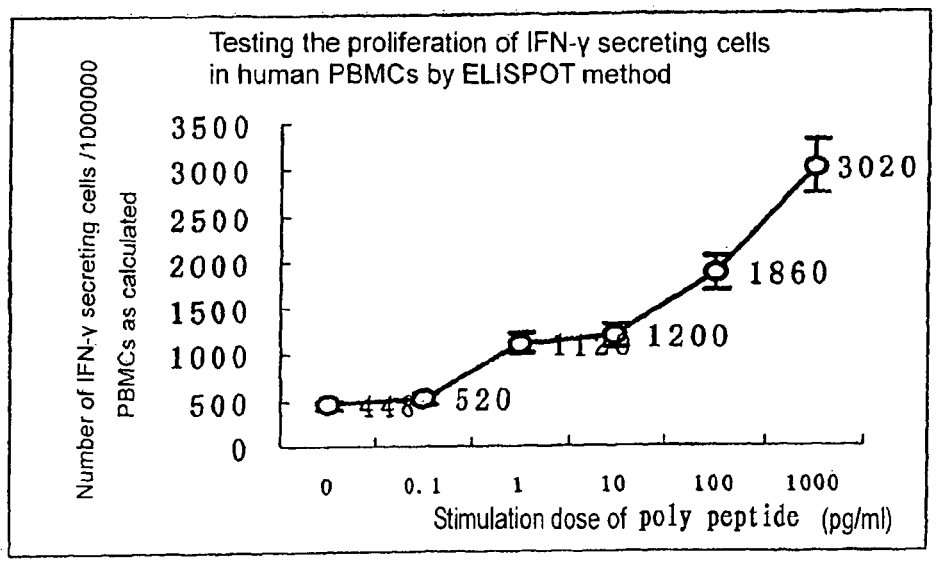

FIG. 4 indicated the effect of inducing cytotoxicity. Peripheral blood mononuclear lymphocytes were separated from fresh peripheral blood of a HLA-A2+ healthy person by the Ficoll-Hypaque method, and were cultured in RPMI1640 culture media (containing 10% fetal calf serum) on a 24-well cell culture plate ($10^6$ cells per cell) in groups. IL-2 (301 U) and the test drugs (10 ng CO, $CH_3CH_2CH=CHCH_2CH=CH(CH_2)_7CO_7KSSQYIKANSKFIGITEGGGDPRVRGLYFPA$) (SEQ ID NO:3) were separately added, and the cells were further cultured for six days. Then the cells were stimulated with IL-2 and the test drug at the same doses once a week for three times. Three days after the last stimulation, antigen-specific effector CTL cells were obtained, and their cytotoxic activities were measured by the standard $^{51}Cr$ release test and compared. Target cells respectively were: 2215 (a human liver carcinomas cell line infected by HBV, which can simulate the function of liver cells infected by HBV), E6 (P815 cells transfected by human HLA-A*0201, which were pre-incubated with CTL epitope peptide antigen), T2 (HLA-A2+ human T and B lymphocytoma cell line, which were pre-incubated with CTL epitope peptide antigen), and the effector cells to target cell ratios (E/T) were: 12.5, 25, 50 and 100, respectively. The results indicated that the test drug could induce the CTL effect in human PBMC, and specifically lyzed and destroyed target cells (A). Twenty-four hours after the last stimulation to HLA-A2+ human PBMC, the effects of the test drug to induce the proliferating INF-γ secreting CTL cells in peripheral blood lymphocytes were measured in the ELISPOT method and compared. The results showed that the test drug could induce the proliferation of IFN-γ secreting cells in human PBMC in a notable dose-effect dependence relation (B, C).

Figure 5A:
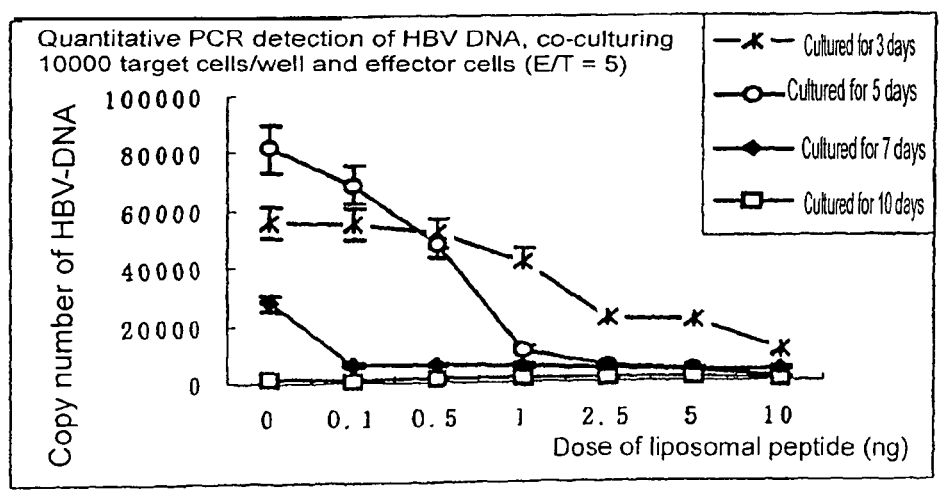
Figure 5B:
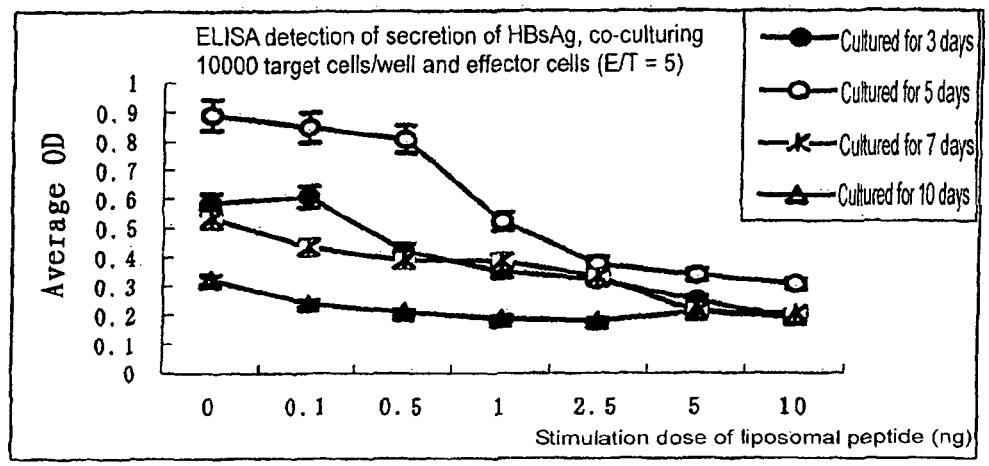
Figure 5C:
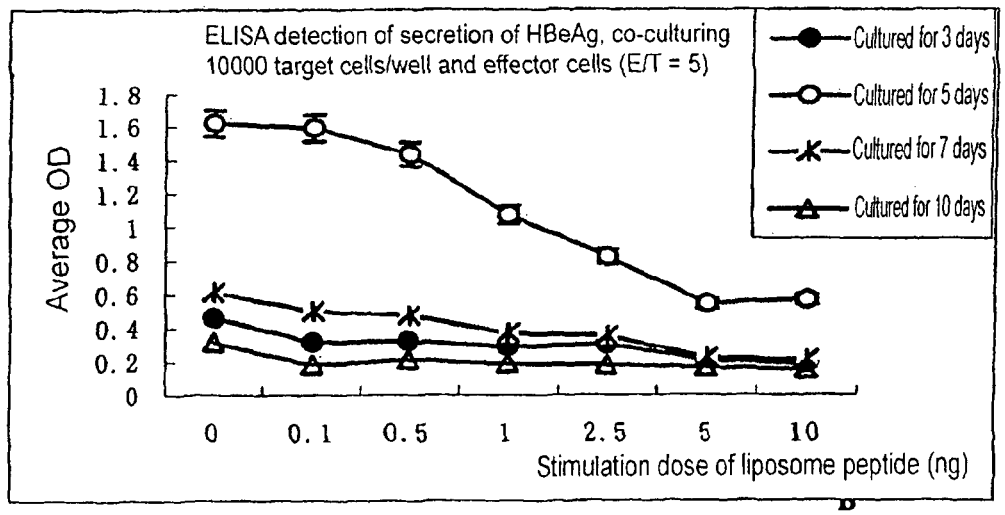
Figure 6A:
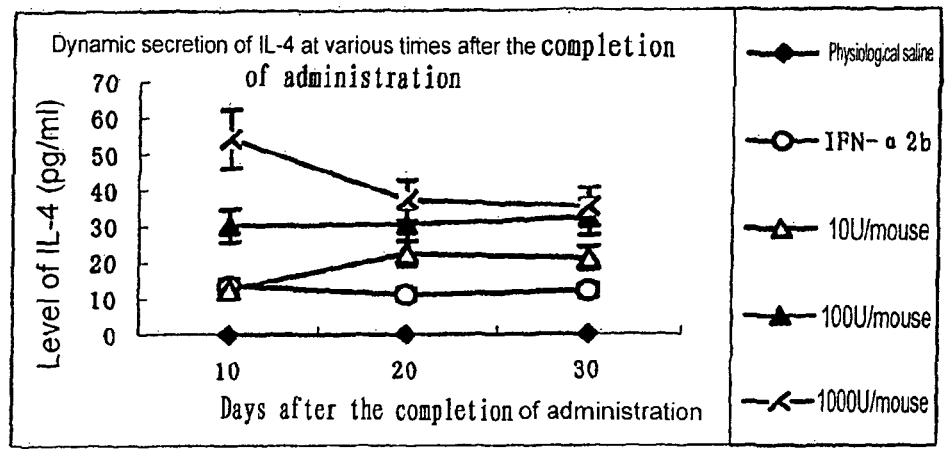
Figure 6B:
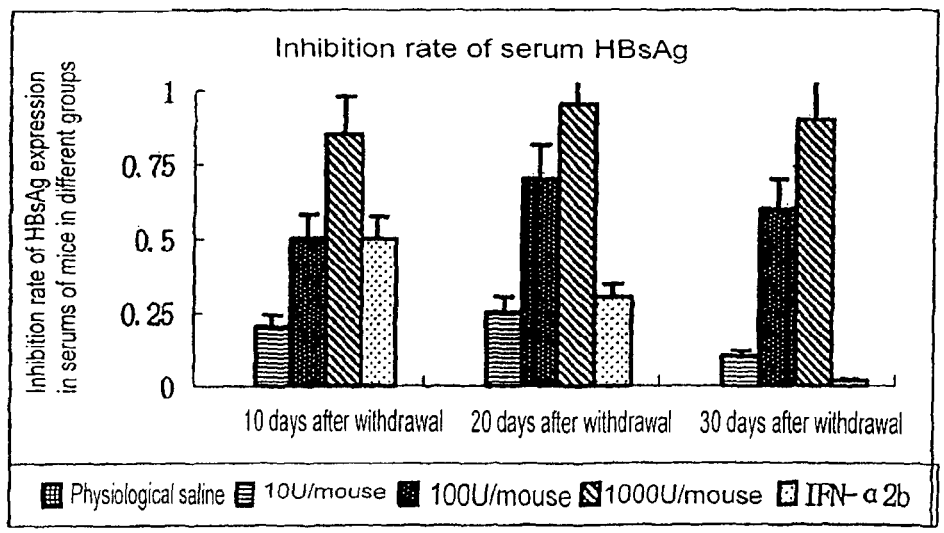
Figure 6C:
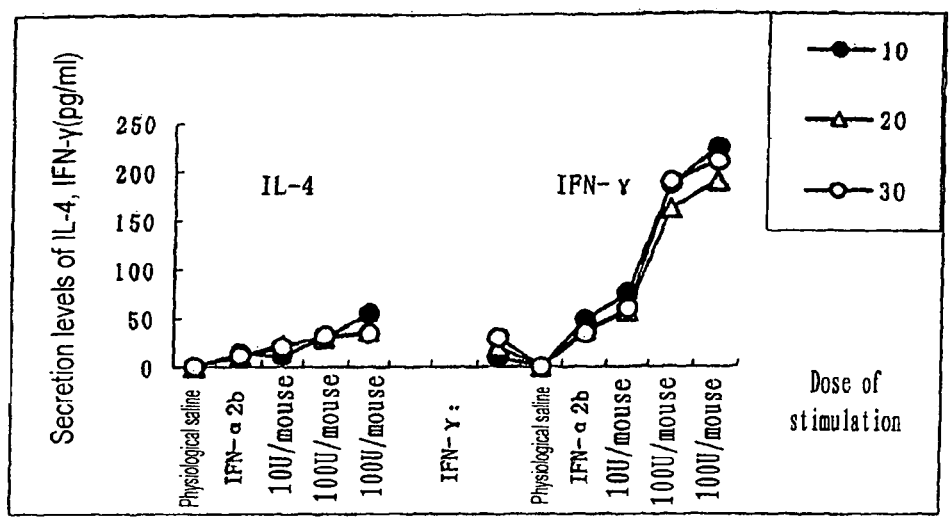
Figure 6D:
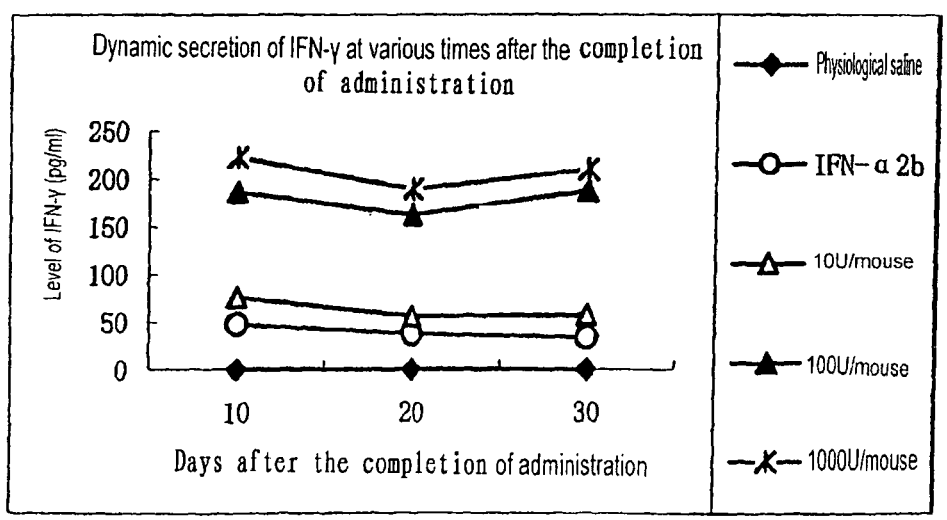
Figure 6E:
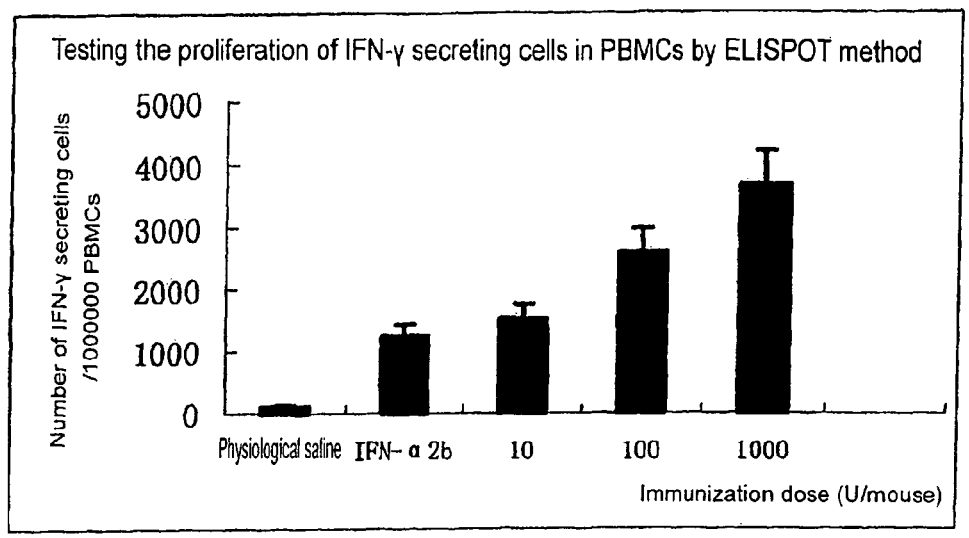
Figure 6F:
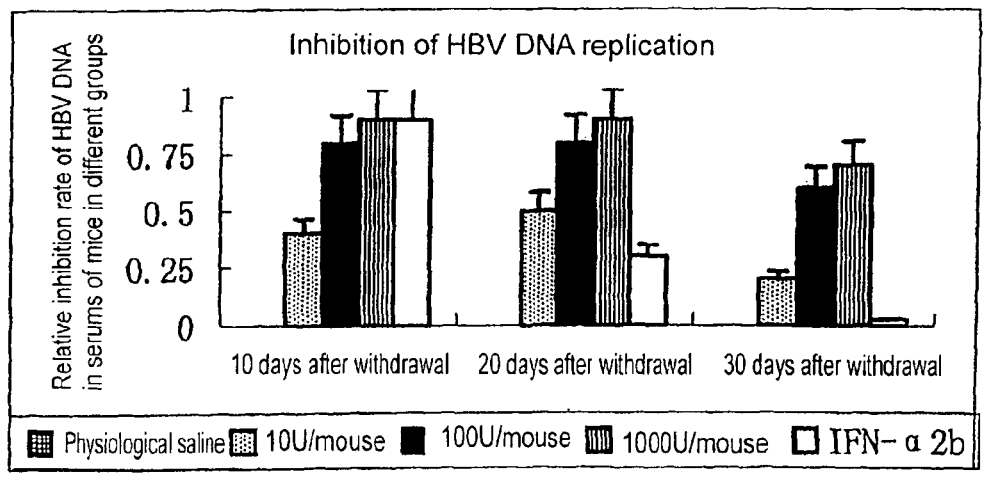

FIG. 5 indicated the antiviral effects of the immunogen of the present invention. Peripheral blood mononuclear lymphocytes were separately isolated from fresh peripheral bloods of a HLA-A2+HBV carrier, a patient suffering from acute hepatitis, and a patient suffering from chronic hepatitis, and were subjected to virus inhibition tests to measure the copy numbers of HBV-DNA (A) and secretion levels of HBeAg and HBsAg in the supernatant (B, C). The results showed that with the increase of co-culture time, the expression/replication of HBV-DNA, HBsAg and HBeAg were inhibited in an obvious dose-effect dependence relation, indicating that the induction of HLA-A2+ human PBMC by the test drug ($CH_3(CH_2)_{14}COKSSQYIKANSKFIGITEAAAFLPSD-FFPSVGGGCTKPTDGNCT$) (SEQ ID NO:4) occurred in an obvious dose-effect dependence manner.

FIG. 6: HBV-DNA transgenic mice (ayw type Kunming mice transfected with the complete gene of HBV (1.3 Kb) were grouped randomly, and each group had five mice. The mice were administered subcutaneously with one of three doses (namely, 10, 100 and 1000 U/mouse) below both costal regions and at both postpede palmas, and the immunizations were enhanced once a week for three times. INF-α2b (15000 U/mouse) was included as a positive control drug, and physiological saline was included as negative control drug. Thirty days after the end of the administration, spleens were removed from mice, and spleen lymphocytes were isolated and stimulated with 10 ng/ml test drug in vitro for three days. The levels of cytokines such as IFN-γ, IL-4, etc. in supernatant were measured by the ELISA method, and the activity of the test drug ($CH_3(CH_2)_{14}COKSSQYIKANSKFIG-ITEAAASIVSPFIPLLGGGDPRVRGLYFPA$) (SEQ ID NO:5) for inducing the differentiation of T cells into Th1/Th2 type was analyzed. The results showed a strong secretion of IFN-γ, and the IL-4 secretion did not exhibit an obvious dose-effect dependence relation (A, B, C). The expression frequency of IFN-γ secreting cells in peripheral blood lymphocytes was measured by the ELI-SPOT method in said supernatant. The results showed that on the 30th day after the end of immunization, the expression frequency of IFN-γ secreting cells in peripheral blood lymphocytes increased with the increase of immunogen dose, wherein the immunization doses of 100 and 1000 U/mouse resulted in an obvious increase of expression frequency of IFN-γ secreting cells in peripheral blood lymphocytes in vivo, with the highest 3660 IFN-γ secreting cells/$10^6$ PBMC being detected. In the group of administration with IFN-α2b, the highest 1250 IFN-γ secreting cells/$10^6$ PBMC (D) were detected. On the 10th, 20th and 30th day after the end of the three immunizations, bloods were removed, serum isolated, and the contents of HBsAg and HBV-DNA in the serum were separately measured by the ELISA method and quantitative PCR method. The results showed that said test drug could result in an obvious decrease of the levels of surface antigen secretion (C) level and HBV-DNA replication (F) level in a dose-dependent manner.

DETAILED DESCRIPTION OF THE PRESENT INVENTION

The present invention provides contents in the following aspects:

An immunogen, characterized in that said immunogen comprises a polypeptide sequence comprising amino acid sequence 1, amino acid sequence 2 and amino acid sequence 3 covalently linked together by linking peptides consisting of several amino acid residues; said amino acid sequence 1 is the sequence of a Th cell epitope; said amino acid sequence 2 is the sequence of a CTL epitope from hepatitis B virus; and said amino acid sequence 3 is the sequence of a B cell epitope from hepatitis B virus.

Said amino acid sequence 1 is the amino acid sequence of position 830-843 of the Th cell epitope from tetanus toxoid or variant sequences thereof, or the universal Th cell epitope PADRE; said amino acid sequence 2 is the amino acid sequence of positions 18-27 of the HBV core antigen or variant sequences thereof, the amino acid sequence of position 141-151 of the HBV core antigen or variants sequences thereof, the amino acid sequence of position 117-125 of the HBV core antigen or variant sequences thereof, the amino acid sequence of position 88-94 of the HBV core antigen or variant sequences thereof, the amino acid sequence of position 88-96 of the HBV core antigen or variant sequences thereof, the amino acid sequence of position 183-191 of the HBV surface antigen or variant sequences thereof, the amino acid sequence of position 201-210 of the HBV surface antigen or variant sequences thereof, the amino acid sequence of position 204-212 of the HBV surface antigen or variant sequences thereof, the amino acid sequence of position 370-379 of the HBV surface antigen or variant sequences thereof, the amino acid sequence of position 251-259 of the HBV surface antigen or variant sequences thereof, the amino acid sequence of position 260-269 of the HBV surface antigen or variant sequences thereof, the amino acid sequence of position 335-342 of the HBV surface antigen or variant sequences thereof, the amino acid sequence of position 338-347 of the HBV surface antigen or variant sequences thereof, the amino acid sequence of position 348-357 of the HBV surface antigen or variant sequences thereof, the amino acid sequence of position 378-387 of the HBV surface antigen or variant sequences thereof; the amino acid sequence of position 10-17 of the Pre S1 antigen or variant sequences thereof, the amino acid sequence of position 109-123 of the Pre S2 antigen or variant sequences thereof, the amino acid sequence of position 152-161 or variant sequences thereof; the amino acid sequence of position 92-100 of the HBx antigen or variant sequences thereof, the amino acid sequence of position 99-108 of the HBx antigen or variant sequences thereof, the amino acid sequence of position 115-123 of the HBx antigen or variant sequences thereof, the amino acid sequence of position 133-141 of the HBx antigen or variant sequences thereof; the amino acid sequence of position 61-69 of the Pol antigen or variant sequences thereof, the amino acid sequence of position 455-463 of the Pol antigen or variant sequences thereof, the amino acid sequence of position 575-583 of the Pol antigen or variant sequences thereof, the amino acid sequence of position 773-782 of the Pol antigen or variant sequences thereof, the amino acid sequence of position 803-811 of the Pol antigen or variant sequences thereof, the amino acid sequence of position 756-764 of the Pol antigen or variant sequences thereof, the amino acid sequence of position 816-824 of the Pol antigen or variant sequences thereof, the amino acid sequence of position 655-663 of the Pol antigen or variant sequences thereof, the amino acid sequence of position 551-559 of the Pol antigen or variant sequences thereof, the amino acid sequence of position 772-780 of the Pol antigen or variant sequences thereof, the amino acid sequence of position 502-510 of the Pol antigen or variant sequences thereof, the amino acid sequence of position 538-546 of the Pol antigen or variant sequences thereof, the amino acid sequence of position 642-650 of the Pol antigen or variant sequences thereof, the amino acid sequence of position 646-654 of the Pol antigen or variant sequences thereof; and said amino acid sequence 3 is the amino acid sequence of position 14-24 of the B cell epitope from HBV Pre-S2 or variant sequences thereof, or determinant a of HBS antigen.

Said amino acid sequence 1 is QYIKANSKFIGITE (SEQ ID NO:6) or variant sequences thereof, PADRE (SEQ ID NO:7) or variant sequences thereof; said amino acid sequence 2 is PLGFFPDH (SEQ ID NO:8) or variant sequences thereof, MQWNSTALHQALQDP (SEQ ID NO:9) or variant sequences thereof, SILSKTGDPV (SEQ ID NO:10) or variant sequences thereof, VLQAGFFLL (SEQ ID NO:11) or variant sequences thereof, FLLTRILTI (SEQ ID NO:12) or variant sequences thereof, FLGGTPVCL (SEQ ID NO:13) or variant sequences thereof, LLCLIFLLV (SEQ ID NO:14) or variant sequences thereof, LLDYQGMLPV (SEQ ID NO:15) or variant sequences thereof, WLSLLVPFV (SEQ ID NO:16) or variant sequences thereof, GLSPTVWLSV (SEQ ID NO:17) or variant sequences thereof, KVLHKRTLGL (SEQ ID NO:18) or variant sequences thereof, VLHKRTLGL (SEQ ID NO:19) or variant sequences thereof, GLSAMSTTDL (SEQ ID NO:20) or variant sequences thereof, CLFKDWEEL (SEQ ID NO:21) or variant sequences thereof, VLGGCRHKLV (SEQ ID NO:22) or variant sequences thereof, FLPSDFFPSV (SEQ ID NO:23) or variant sequences thereof, STLPETTVVRR (SEQ ID NO:24) or variant sequences thereof, EYLVSFGVW (SEQ ID NO:251 or variant sequences thereof, GLYSSTVPV (SEQ ID NO:26) or variant sequences thereof, GLSRYVARL (SEQ ID NO:27) or variant sequences thereof, FLLSLGIHL (SEQ ID NO:28) or variant sequences thereof, ILRGTSFVYV (SEQ ID NO:29) or variant sequences thereof, SLYADSPSV (SEQ ID NO:30) or variant sequences thereof, KYTSFPWLL (SEQ ID NO:31) or variant sequences thereof, SLYADSPSV (SEQ ID NO:32) or variant sequences thereof, ALMPLYACI (SEQ ID NO:33) or variant sequences thereof, YMDDVVLGA (SEQ ID NO:34) or variant sequences thereof, WILRGTSFV (SEQ ID NO:35) or variant sequences thereof, KLHLYSHPI (SEQ ID NO:36) or variant sequences thereof, FTQAGYPAL (SEQ ID NO:37) or variant sequences thereof, SLNFLGGTTV (SEQ ID NO:38) or variant sequences thereof, LLDYQGMLPV (SEQ ID NO:39) or variant sequences thereof, LLVPFVQWFV (SEQ ID NO:40) or variant sequences thereof, GLSPTVWLSV (SEQ ID NO:41) or variant sequences thereof, LLPIFFCLWV ISEQ ID NO:42) or variant sequences thereof, YVNTNMG (SEQ ID NO:43) or variant sequences thereof, YVNTNMGLK (SEQ ID NO:44) or variant sequences thereof, SILSKTGDPV (SEQ ID NO:45) or variant sequences thereof, GLSPTVWLSV (SEQ ID NO:46) or variant sequences thereof, or SIVSPFIPLL (SEQ ID NO:47) or variant sequences thereof; said amino acid sequence 3 is DPRVRGLYFPA (SEQ ID NO:48) or variant sequences thereof, or CTKPTDGNCT (SEQ ID NO:49) or variant sequences thereof.

The said immunogen, characterized in that the linking peptide consists of 3-7 amino acid residues.

The said immunogen, characterized in that the linking peptide is AAA, SSS or GGG.

The said immunogen, characterized in that the linking order of the amino acid sequence 1, the amino acid sequence 2 and the amino acid sequence 3 is amino acid sequence 1-amino acid sequence 2-amino acid sequence 3, amino acid sequence 1-amino acid sequence 3-amino acid sequence 2, amino acid sequence 2-amino acid sequence 1-amino acid sequence 3, amino acid sequence 2-amino acid sequence 3-amino acid sequence 1, amino acid sequence 3-amino acid sequence 1-amino acid sequence 2, or amino acid sequence 3-amino acid sequence 2-amino acid sequence 1.

The said immunogen, characterized in that the said immunogen further comprises several modifying groups which can be alkylcarbonyl groups, or alkenylcarbonyl groups.

The said immunogen, characterized in that the said immunogen further comprises two modifying groups.

The said immunogen, characterized in that the said immunogen further comprises one modifying group.

The said immunogen, characterized in that the said alkylcarbonyl group is one to five alkylcarbonyl groups selected from a group consisting of $CH_3(CH_2)_{10}CO—$, $CH_3(CH_2)_{12}CO—$, $CH_3(CH2)_{14}CO—$ and $CH_3(CH_2)_{16}CO—$; the said alkenylcarbonyl group is one to five alkenylcarbonyl groups selected from a group consisting of $CH_3(CH_2)_7CH=CH(CH_2)_7CO—$, $CH_3CH_2CH=CHCH_2CH=CH—(CH_2)_7CO—$ and $CH_3CH_2CH=CHCH_2CH=CH(CH_2)CH=CH(CH_2)_7CO—$.

The said immunogen, characterized in that the said modifying group is covalently linked to any amino acid residue of the polypeptide sequence.

The said immunogen, characterized in that the said modifying group is covalently linked to N-terminal α-amino group, C-terminal α-carboxyl group or any side chain group of amino acid residue of said polypeptide sequence.

The said immunogen, characterized in that the said modifying group is linked to the N-terminal α-amino group of said polypeptide sequence via a linking peptide KSS, wherein the N-terminal α-amino group is linked to the C-terminal of the linking peptide KSS via a peptide bond, and said modifying group is covalently linked to the ϵ-amino group of the linking peptide KSS.

The said immunogen, characterized in that the said modifying group is covalently linked to an amino group, carboxyl group or hydroxyl group on said side chain group.

The said immunogen, characterized in that the said modifying group is covalently linked to the ϵ-amino group of the N-terminal lysine.

The said immunogen, characterized in that the α-amino group of said linking peptide KSS is further covalently linked to one of said modifying groups.

The said immunogen, characterized in that its primary structure is $CH_3(CH_2)_{10}COKSSPADREGGGSLNFLGGT$-TVSSSDPRVRGLYFPA (SEQ ID NO:50).

The said immunogen, characterized in that its primary structure is $CH_3(CH_2)_{14}COKSSQYIKANSKFIG$-ITEAAALLCLIFLLVGGGDPRVRGLYFPA (SEQ ID NO:51).

The said immunogen, characterized in that its primary structure is $CH_3(CH_2)_{16}COKSSPADREAAALLDYQGM$-LPVGGGDPRVRGLYFPA (SEQ ID NO:52).

The said immunogen, characterized in that its primary structure is $CH_3(CH_2)_7CH=CH(CH_2)—CO$, $CH_3CH_2CH—CHCH_2CH=CH(CH_2)_7$ $CO_7KSSQYIKANSKFIGITEGGG$ (SEQ ID NO:53).

The said immunogen, characterized in that its primary structure is $CH_3CH_2CH=CHCH_2CH=CH(CH_2)CH=CH(CH_2)_7COFLPSDFFPSVAAADPRVRGLYFPA$ (SEQ ID NO:54).

The said immunogen, characterized in that its primary structure is $CH_3CH_2CH=CHCH_2CH=CH(CH_2)CH=CH(CH_2)_7COKSSPADREGGGWLSLLVPFVSS$ SD PRVRGLYFPA (SEQ ID NO:55).

The said immunogen, characterized in that its primary structure is $CH_3(CH_2)_{14}COKSSQYIKANSKFIG$-ITEAAAFLPSDFFPSVGGGDPRVRGLYFPA (SEQ ID NO:1).

The said immunogen, characterized in that its primary structure is $CH_3(CH_2)_{14}COKSSPADREAAAFLPSDFFPS$-VGGGDPRVRGLYFPA (SEQ ID NO:56).

The said immunogen, characterized in that its primary structure is $CH_3(CH_2)_{14}COKSSPADREGGGLLVPFVQW$-FVSSSDPRVRGLYFPA (SEQ ID NO:57).

The said immunogen, characterized in that its primary structure is $CH_3(CH_2)_{14}COKSSPADREAAAGL$-SPTVWLSVGGGDPRVRGLYFPA (SEQ ID NO:58).

The said immunogen, characterized in that its primary structure is $CH_3(CH_2)_{16}COKSSPADREAAALLPIFF$-CLWVGGGDPRVRGLYFPA (SEQ ID NO:59).

The said immunogen, characterized in that its primary structure is $CH_3(CH_2)_{16}COKSSQYIKANSKFIG$-ITEAAAYVNTNMGGGGDPRVRGLYFPA (SEQ ID NO:60).

The said immunogen, characterized in that its primary structure is $CH_3(CH_2)_{16}COKSSQYIKANSKFIG$-ITEAAAFLPSDFFPSVGGGDPRVRGLYFPA (SEQ ID NO:74)

The said immunogen, characterized in that its primary structure is $CH_3(CH_2)_{14}COKSSQYIKANSKFIGITEGGG$-FLPSDFFPSVSSSDPRVRGLYFPA (SEQ ID NO:61).

The said immunogen, characterized in that its primary structure is $CH_3(CH_2)_{14}COKSSQYIKANSKFIG$-ITEAAAYVNTNMGLKGGGDPRVRGLYFPA (SEQ ID NO:62).

The said immunogen, characterized in that its primary structure is $CH_3(CH_2)_{14}COKSSQYIKANSKFIGITEAAA$-PLGFFPDHGGGDPRVRGLYFPA (SEQ ID NO:63).

The said immunogen, characterized in that its primary structure is $CH_3(CH_2)_{14}COKSSQYIKANSKFIG$-ITEAAAMQWNSTALHQALQDPGGGDPRVRGLYFPA (SEQ ID NO:64)

The said immunogen, characterized in that its primary structure is $CH_3(CH_2)_{14}COKSSPDAREAAASILSKTGD$-PVGGGDPRVRGLYFPA (SEQ ID NO:65).

The said immunogen, characterized in that its primary structure is $CH_3(CH_2)_{16}COKSSPADREAAAVLQAGF$-FLLGGGDPRVRGLYFPA (SEQ ID NO:66).

The said immunogen, characterized in that its primary structure is $CH_3(CH_2)_{16}COKSSPADRESSSFLLTRILT$-IGGGDPRVRGLYFPA (SEQ ID NO:67).

The said immunogen, characterized in that its primary structure is $CH_3(CH_2)_{16}COKSSPADREAAAFLGGTPV$-CLGGGDPRVRGLYFPA (SEQ ID NO:68).

The said immunogen, characterized in that its primary structure is $CH_3(CH_2)_{14}COKSSQYIKANSKFIGITEAAA$-GLSPTVWLSVGGGDPRVRGLYFPA (SEQ ID NO:69).

The said immunogen, characterized in that its primary structure is $CH_3(CH_2)_{14}COKSSQYIKANSKFIGITEAAA$-SIVSPFIPLLGGGDPRVRGLYFPA (SEQ ID NO:5).

The said immunogen, characterized in that its primary structure is $CH_3(CH_2)_{16}COKSSPADREAAASTLPETTV$-VRRGGGDPRVR GLYFPA (SEQ ID NO:70).

The said immunogen, characterized in that its primary structure is $CH_3(CH_2)_{14}COKSSQYIKANSKFIG$-ITEAAAFLPSDFFPSVGGGCTKPTDGNCT (SEQ ID NO:4).

A method for designing, screening and synthesizing said immunogen, comprising epitope-based vaccine design (EBVD), molecular simulation, molecular design, screening system and solid-phase synthesis of polypeptide, wherein the molar ratio of resin to each amino acid or palmitic acid feed is from 1:2 to 1:8, the di-coupling is used for linking arginine, asparagin and palmitic acid component, and the reaction temperature is from 20 to 40° C.

Said molar ratio is 1:4, and the reaction temperature is 30° C.

A method for preparing said immunogen, characterized in that said method comprises the following steps: (1) synthesizing the immunogen-resin by polypeptide solid synthesis, wherein said immunogen-resin represents the immunogen bound to resin; (2) cleaving said immunogen-resin to obtain a cleaved solution; (3) preliminarily purifying the cleaved solution of the step (2) by size exclusion chromatography; and (4) purifying by reversed phase chromatography to obtain the immunogen.

The said method, characterized in that TFA cleaving solution is used in the step (2), and the cleaving conditions are as follows: the concentration of the immunogen-resin is lower than 100 mg/ml, the reaction temperature is from 15 to 50° C., and the reaction time is from 0.5 to 3 hours.

The said method, characterized in that said TFA cleaving solution is composed of 0.75 g phenol, 0.25 ml dithioglycol, 0.5 ml phenyl methyl thioether, 0.5 ml deionized water, and 10.0 ml TFA; and said cleaving conditions are as follows: the concentration of the immunogen-resin is 40.00 mg/ml, the reaction temperature is 25° C., and the reaction time is 1.5 hours.

The said method, characterized in that Sephadex LH20 is used in the size exclusion chromatography in the step (3), and dimethyl sulfoxide as the mobile phase.

The said method, characterized in that POROS 50R1, POROS 50R2, SOURCE 30 RPC or Delta Pak C18 is used in the reversed phase chromatography in the step (4).

The said method, characterized in that a gradient elution is employed in the reversed phase chromatography in the step (4), wherein the mobile phase is an aqueous solution of acetonitrile/TFA, acetonitrile/HCl, ethanol/TFA, ethanol/HCl or ethanol/phosphoric acid.

The said method, characterized in that the column temperature in said reversed phase chromatography is from 20 to 60° C.

The said method, characterized in that the column temperature in said reversed phase chromatography is from 28 to 40° C.

The said method, characterized in that the column temperature in said reversed phase chromatography is from 32 to 36° C.

The said method, characterized in that the column temperature of said reversed phase chromatography is 34° C.

Use of said immunogen in the manufacture of a vaccine or a medicament for treatment of the chronic HBV persistent infection state and associated secondary diseases such as liver cirrhosis, liver cancer, etc.

The said use, characterized in that said chronic HBV persistent infection state occurs in patients with chronic hepatitis B or carriers of hepatitis B virus.

A vaccine for treatment of hepatitis B, characterized in that said vaccine comprises the above-mentioned immunogen.

A vaccine for treatment of hepatitis B, characterized in that said vaccine comprises said immunogen and pharmaceutically acceptable auxiliary materials, adjuvants and/or carriers.

The said vaccine for treatment of hepatitis B, characterized in that said vaccine is in any pharmaceutically acceptable form.

The said vaccine for treatment of hepatitis B, characterized in that the formulation of said vaccine is injection formulation, percutaneous formulation, oral formulation, inhalant formulation or suppository formulation.

The said vaccine for treatment of hepatitis B, characterized in that said vaccine is in ethanol solution dosage form, suspension dosage form, liquid liposome dosage form or lyophilized liposome dosage form.

The said vaccine for treatment of hepatitis B, characterized in that said liquid liposome dosage form or lyophilized liposome dosage form comprises phospholipids.

The said vaccine for treatment of hepatitis B, characterized in that said liquid liposome dosage form or lyophilized liposome dosage form further comprises cholesterol.

The said vaccine for treatment of hepatitis B, characterized in that said liquid liposome dosage form or lyophilized liposome dosage form further comprises vitamin E.

The said vaccine for treatment of hepatitis B, characterized in that said liquid liposome dosage form or lyophilized liposome dosage form further comprises palmitic acid.

The said vaccine for treatment of hepatitis B, characterized in that the molar ratio between immunogen:phospholipids:cholesterol:vitamin E:palmitic acid is 0.1-0.5:40-80:0-40:0-10:0-10.

The said vaccine for treatment of hepatitis B, characterized in that the molar ratio between immunogen phospholipids:cholesterol:vitamin E:palmitic acid is 0.2-0.4:60:20:6:6.

The said vaccine for treatment of hepatitis B, characterized in that the molar ratio of immunogen: phospholipids:cholesterol:vitamin E:palmitic acid in the vaccine is 0.3-0.36:60:20:6:6.

The said vaccine for treatment of hepatitis B, characterized in that said phospholipids are soybean phospholipid or lecithin.

A method for preparing the above-mentioned vaccine for treatment of hepatitis B, characterized in that said method comprises using a two-emlsifying method to prepare the liposome.

The said vaccine for treatment of hepatitis B, characterized in that said lyophilized liposome dosage form further comprises human albumin, mannitol and phosphates. The said vaccine for treatment of hepatitis B, characterized in that said lyophilized liposome dosage form comprises said immunogen, phospholipid, cholesterol, palmitic acid, vitamin E, mannitol, human albumin, $KH_2PO_4$ and $Na_2HPO_4$ in a molar ratio of 0.01-0.1:5-15: 1-7:0.5-1.5:0.5-1.5:70-150:0.1-0.3:1-10: 1-10.

A further object of the present invention is to provide a method for designing, screening and preparing the said immunogen or vaccine of the present invention.

The present invention firstly establishes the epitope-based vaccine design (EBVD). The vaccine is designed and selected by EBVD based on the epitope map of hepatitis B virus, in terms of different epitope types, different antigen sources of the epitopes, different linking orders, different chemical modifying groups, etc. Immunogens with the above-mentioned backbones were firstly developed, which, on the one hand, could stimulate the proliferation of lymphocytes in human peripheral blood, the activation of Th1 and the HBV-specific CTL reaction, and inhibit the replication of HBV, the effectiveness being increased by at least 200 folds than using single epitope polypeptide; the other hand, could effectively stimulate the activation of Th1 and the HBV-specific CTL reaction, and inhibit the replication of HBV in HBV transgenic mice in vivo. The experimental results indicate that said immunogens can be developed into a novel vaccine or medicament for treatment of hepatitis B and associated secondary diseases such as liver cirrhosis, liver cancer, etc.

Said immunogen molecules could be prepared by a solid-phase synthesis. The optimal temperature, feed ratio, method and time for cleaving peptide-resin, purification conditions, etc. are determined. In the method of the present invention, the optimal temperature is 30-40° C.; the α, β, γ, δ components are synthesized continuously by using the HOBT/DCC coupling strategy; and R, N, and a are synthesized by the double coupling method; the optimal molar ratio of the starting materials to resin is 4:1; the average coupling efficiency is above 99.5%; and the trifluoroacetic acid method is employed for cleaving the peptide-resin, the optimum cleaving time being 90 minutes.

In the method of the present invention, the purification is carried out in a two-step way: (1) using size exclusion chromatography for preliminary purification, wherein dimethyl sulphoxide (DMSO) is used as mobile phase, and the optimum column temperature is 20-40° C.; and (2) using reversed chromatography for further purification. The optimal conditions for loading sample, the preferred packing material, the optimal column temperature, etc. are studied. In the present invention, the packing material is preferably POROS 50 R1, and the optimal column temperature is 22-34° C.

After comparing ethanol solution dosage form, liposome suspension dosage form and liposome lyophilized dosage form, it is proven that the liposome dosage forms are superior to the ethanol solution dosage form in terms of the induction of Th1 activation and CTL activity, as well as the alleviation of the pain caused by subcutaneous injection. The liposome lyophilized dosage form is obviously superior to the liposome suspension dosage form in terms of stability.

In the present invention, the optimal formulation of liposome injection dosage form of said immunogen is determined and selected by using a $L_9(3^4)$ orthogonal design, wherein said formulation comprises said immunogen, soybean phospholipid, palmitic acid, vitamin E and/or cholesterol.

Further, the effects of various conditions on the formation, encapsulation rate and particle size distribution of liposome are compared. The conditions and diagram for preparing liposome are determined.

copy numbers of HBV DNA and the titres of HBsAg and HbeAg or even eliminate them. This effect is more than 200 times higher than that when mono-epitope polypeptide is used.

EXAMPLES

1. Using EBVD to Design and Screen the Number and Order of the Epitopes of Tri-Epitope Vaccine (Synthesized Peptide) for Treatment of Hepatitis B Based on the hepatitis B epitope map, the EBVD is used to design and screen epitope components according to different epitope types, different sources of antigen epitopes, different linking orders, different chemical modifying groups, etc., wherein the sources of antigen epitopes include: prevalent B cell epitopes from s antigen, e antigen and c antigen of HBV, T helper cell (Th) epitopes, cytotoxic T cell (CTL) epitopes, universal Th cell epitopes from other antigen sources, and epitope-modifying groups. As to the epitope-modifying groups, single-chain fatty acids having been proved in prior art documents to exhibit immune promoting activity and the glycosyl groups which have been proven by the inventors are encompassed. In the present invention, modified linear mono-epitope type, branched mono-epitope type (2, 4, 8 branches), chimeric CTL epitope-Th cell epitope type, modified chimeric CTL epitope-Th cell epitope type, chimeric B cell epitope-CTL epitope-Th cell epitope type and modified chi-

```
Raw liquor --Ultrafiltration, concentration--> Concentrated liquor    High purity nitrogen Lipoid solution --Sterilization, filtration--> Suspension, pouring in    40° C., suspending
                                              Emulsion (W/O)              Injection water 40° C., suspension              Ultrafiltration, concentration, dialysis
Emulsion (W/OW) --> Liposome suspension --> Liposome concentrate
```

The third object of the present invention is to provide use of the immunogens of the present invention in the manufacture of a vaccine or medicament for treatment of chronic HBV persistent infection state and associated secondary diseases such as liver cirrhosis, liver cancer, etc.

Said immunogens and dosage forms thereof are used for immunization via any known immunization route, such as subcutaneous injection, intradermal injection, peritoneal injection, intravenous injection, etc. The immunization dose may be from 0.01 nmol to 20 nmol. Additional adjuvants may not be used. When they are used for immunizing mice or HLA transgenic mice, they can stimulate the activation and proliferation of lymphocytes, the Th1 activation and CTL response. When they are used for immunizing HBV transgenic mice, they can stimulate the activation and proliferation of lymphocytes, the Th1 activation and CTL response in a dose-dependent manner, inhibit HBV replication, and result in the decrease of the copy numbers of HBV DNA in blood and the decrease or elimination of HBsAg and HBeAg titers. These effects cannot be achieved when mono-epitope polypeptide or multi-epitope polypeptide is used alone. When they are used for stimulating human peripheral blood mononuclear cells, they can stimulate the activation and proliferation of lymphocytes, the Th1 activation and CTL response in a dose-dependent manner. The CTL response can kill HepG2.2.1.5 cells and E6 cells, inhibit HBV replication, and reduce the meric B cell epitope-CTL epitope-Th cell epitope type are used. The epitopes are linked together through -A-A-A- or -G-G-G- that has been proven to exhibit no effect on antigenicity (immunogenicity). Thus, more than 200 structures are obtained. The similarity between the structures of the designed antigen polypeptides and the natural antigen is analyzed, and the steric hindrance of complexing with MHC is studied by molecular simulation method at O2 workstation (Insight II software), and the immunogenicity, physical/chemical and biochemical properties of the antigen polypeptides are analyzed and aligned.

The designed immunogens are synthesized by chemical synthesis methods. Firstly, the most probable structures according to the computer alignment and in theory are synthesized, and then functionally screened in vitro. The screening in vitro comprises: inducing the Th1 activation of peripheral blood mononuclear cells, inducing the HBV-specific CTL, inhibiting HBsAg and HBeAg on HepG2.2.1.5 cells with polypeptide antigen-specific CTL, etc. The designed structures are optimized, improved and synthesized in the next cycle bused on the results of functional tests in vitro. The structures selected out in the in vitro tests are further screened in in vivo tests, the screening comprising: inducing the Th1 activation in Balb/C mice, inhibiting virus replication in HBV transgenic mice, conducting acute toxicity tests in mice, etc.

After so many screening and comparison cycles, it is found that polypeptide antigens having 3 epitopes are better candidates. Further screening indicates that the tri-epitope polypeptide antigens are superior to mono- or di-epitope polypeptide antigens, and are not significantly different from polypeptide antigens having four or more epitopes (see Table 3). Among tri-epitope molecules of different epitope combinations, ϵPA44 achieves the best effect (see Table 4). The in vivo and in vitro tests indicate that the convalent modification by palmitic acid gives better effects among various chemical modifications. The monoclonal antibody and peptide probe tests prove that the immune specificity of epitopes in the immunogens does not change due to the selection of certain linking orders. The results of screening are shown in Table 1 and Table 2.

TABLE 1

The screening of epitope number of (synthesized peptide) vaccines for treatment of hepatitis B

| Epitope number | Molecule simulation | Th1 activation | Lymphocyte proliferation | CTL response | Effect of viral inhibition |
|---|---|---|---|---|---|
| 1C | +++ | ± | + | ++ | ++ |
| 1C-1T | +++ | ++ | +++ | +++ | +++ |
| 1C-1B | ++ | + | + | ++ | + |
| 1B-IT | − | + | ++ | − | − |
| 1C-1B-1T | +++ | ++ | ++++ | ++++ | +++ |
| 2C-1B-1T | ± | ++ | ++++ | +++ | +++ |
| 2T-1B-1C | ± | ++ | +++ | +++ | +++ |

* In the column of "Epitope number", immunogens consisting of three types of epitope (including different combination orders) are listed, wherein C represents CTL epitope, B represents B-cell epitope, T represents Th-cell epitope, and digital figures represent the number of epitope. This table shows the results of in vitro screening.

TABLE 2

Screening of tri-epitope molecules with different epitope combinations

| Epitope combination | Molecular simulation | Th1 activation | Lymphocyte proliferation | CTL response | Effect of viral inhibition |
|---|---|---|---|---|---|
| T-C-B | +++ | ++ | ++++ | ++++ | +++ |
| T-B-C | ++ | ++ | +++ | ++ | ++ |
| C-T-B | ++ | + | ++ | + | ± |
| C-B-T | + | ++ | +++ | ++ | + |
| B-T-C | +++ | ++ | ++++ | +++ | ++ |
| B-C-T | +++ | + | ++ | ++ | + |

* In the column of "Epitope combination", epitopes are listed from N-terminus to C-terminus, wherein C represents CTL epitope, B represents B-cell epitope, T represents Th-cell epitope. This table shows the results of in vitro screening.

2. Solid-Phase Chemical Synthesis of $CH_3(CH_2)_{10}COKSS$-PADRE GGGSLNFLGGTTVSSSDPRVRGLYFPA (SEQ ID NO:50)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, with the loading amount being 1 mM. The side chains were protected as follows: Ser(tBu), Thr(tBu), Tyr(tBu), His(Trt), Gln(Trt), ASP(OtBu), Glu(OtBu), Arg (Pmc). HMP-resin was used as the solid-phase carrier, the loading amount being 0.25 mM. That is to say, the ratio of starting materials/resin was 4:1. The amino acid coupled to the resin (the first amino acid at the carboxyl terminus of the polypeptide) was activated by the symmetrical anhydride activation method, and the other amino acids and palmitic acid were activated by HOBt/DCC activation method, wherein asparagine, arginine and palmitic acid were di-coupled, and the coupled palmitic acid was not subjected to a deprolection step of removing Fmoc.

Cleavage and deprotection: a mixture solution of TFA, EDT, phenyl methyl thioether, crystalline phenol and ultra-pure water in a certain proportion was used to cleave the peptide from the resin and to cleave the side protection groups from the amino acids, and then a crude peptide product was obtained by precipitation in ethyl ether and rotatory evaporation. The crude peptide product was identified to be about 80% pure through HPLC.

3. Solid-Phase Chemical Synthesis of $CH_3(CH_2)_{14}$COKSSQYIKA NSKFIGITEAAALLCLIFLLVGGGD-PRVRGLYFPA (SEQ ID NO:51)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain were protected as follows: Ser(tBu), Thr(tBu), Tyr(tBu), His(Trt), Gln(Trt), ASP(OtBu), Glu(OtBu), Arg(Pmc). HMP-resin was used as solid-phase carrier, the loading amount being 0.25 mM. That is to say, the ratio of the starting materials/resin was 4:1. The amino acid coupled to the resin (the first amino acid at carboxyl terminus of the polypeptide) was activated by the symmetrical anhydride activation method, and the other amino acids and palmitic acid were activated by HOBt/DCC activation method, wherein asparagine, arginine and palmitic acid were di-coupled, and the coupled palmitic acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 85% pure through HPLC.

4. Solid-Phase Chemical Synthesis of $CH_3(CH_2)_{16}$COKSS-PADREAAA LLDYQGMLPVGGGDPRVRGLYFPA (SEQ ID NO:52)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were starting materials, the loading amount being 1 mM, and the side chains were protected as follows: Ser(tBu), Thr(tBu), Tyr(tBu), His(Trt), Gln(Trt), ASP(OtBu), Glu(OtBu), Arg(Pmc). HMP-resin was used as solid-phase carrier, the loading amount being 0.25 mM. That is to say, the ratio of starting materials/resin was 4:1. The amino acid coupled to the resin (the first amino acid at the carboxyl terminus of the polypeptide) was activated by symmetrical anhydride activation method, and the other amino acids and palmitic acid were activated by the HOBt/DCC activation method, wherein asparagine, arginine and palmitic acid were di-coupled, and the coupled palmitic acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from the amino acids. A crude peptide product was obtained by precipitation in ethyl ether and rotatory evaporation. The crude peptide product was determined to be about 80% pure by HPLC.

5. Solid-Phase Chemical Synthesis of $CH_3(CH_2)_7CH=CH(CH_2)—CO$, $CH_3CH_2CH=CHCH_2CH=CH(CH_2)_7CO_7KSSQYIKANSKFIGITEGGGDPRVRGLYFPA$ (SEQ ID NO:3)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were starting materials, the loading amount being 1 mM, and the side chains were protected as follows: Ser(tBu), Thr(tBu), Tyr (tBu), His(Trt), Gln(Trt), ASP(OtBu), Glu(OtBu), Arg(Pmc). HMP-resin was used as solid-phase carrier, the loading amount being 0.25 mM. That is to say, the ratio of starting materials/resin was 4:1. The amino acid coupled to the resin (the first amino acid at the carboxyl group terminus of the polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 80% pure through HPLC.

6. Solid-Phase Chemical Synthesis of $CH_3CH_2CH=CHCH_2CH=CH(CH_2)CH=CH(CH_2)_7$ COFLPSDFFPSVAAADPRVRGLYFPA (SEQ ID NO:54)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 80% pure through HPLC.

7. Solid-Phase Chemical Synthesis of $CH_3CH_2CH=CHCH_2CH=CH(CH_2)CH=CH(CH_2)_7$ COKSSPADREGGGWLSLLVPFVSSSDPR VRGLYF-PARGLYFPA (SEQ ID NO:71)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 80% pure through HPLC.

8. Solid-Phase Chemical Synthesis of $CH_3(CH_2)_{14}$ COKSSQYIKANS KFIGITEAAAFLPSDFFPSVGGGD-PRVRGLYFPA (SEQ ID NO:1)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 80% pure through HPLC.

9. Solid-Phase Chemical Synthesis of $CH_3(CH_2)_{14}$COKSS-PADREAAA FLPSDFFPSVGGGDPRVRGLYFPA (SEQ ID NO:56)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 80% pure through HPLC.

10. Solid-Phase Chemical Synthesis of $CH_3(CH_2)_{14}COKSS$-PADRE GGGLLVPFVQWFVSSSDPRVRGLYFPA (SEQ ID NO:57)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 75% pure through HPLC.

11. Solid-Phase Chemical Synthesis of $CH_3(CH_2)_{14}COKSS$-PADREAAA GLSPTVWLSVGGGDPRVRGLYFPA (SEQ ID NO:58)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave side protection groups from amino acids, and then a crude peptide product was obtained by precipitation in ethyl ether and rotatory evaporation. The crude peptide product was determined to be about 78% pure through HPLC.

12. Solid-Phase Chemical Synthesis of $CH_3(CH_2)_{16}COKSS$-PADREAAA LLPIFFCLWVGGGDPRVRGLYFPA (SEQ ID NO:59)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 80% pure through HPLC.

13. Solid-Phase Chemical Synthesis of $CH_3(CH_2)_{16}$ COKSSQYIKANSKFI GITEAAAYVNTNMGGGGD-PRVRGLYFPA (SEQ ID NO:60)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 83% pure through HPLC.

14. Solid-Phase Chemical Synthesis of $CH_3(CH_2)_{16}$ COKSSQYIKANSKFI GITEAAAFLPSDFFPSVGGGD-PRVRGLYFPA (SEQ ID NO:74)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/

DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 80% pure through HPLC.

15. Solid-Phase Chemical Synthesis of $CH_3(CH_2)_{14}$ COKSSQYIKAN SKFIGITEGGGFLPSDFFPSVSSSD-PRVRGLYFPA (SEQ ID NO:61)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 80% pure through HPLC.

16. Solid-Phase Chemical Synthesis of $CH_3(CH_2)_{14}$ COKSSQYIKAN SKFIGITEAAAYVNTNMGLKGGGD-PRVRGLYFPA (SEQ ID NO:62)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 81% pure through HPLC.

17. Solid-Phase Chemical Synthesis of $CH_3(CH_2)_{14}$ COKSSQYIKANSK FIGITEAAAPLGFFPDHGGGD-PRVRGLYFPA (SEQ ID NO:64)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 81% pure through HPLC.

18. Solid-Phase Chemical Synthesis of $CH_3(CH_2)_{14}$ COKSSYIKANSK FIGITEAAAMQWNSTALHQALQD-PGGGDPRVRGLYFPA (SEQ ID NO:72)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 86% pure through HPLC.

19. Solid-Phase Chemical Synthesis of $CH_3(CH_2)_{14}$ COKSSPDAREAAA ILSKTGDPVGGGDPRVRGLYFPA (SEQ ID NO:65)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 78% pure through HPLC.

20. Solid-Phase Chemical Synthesis of $CH_3(CH_2)_{16}$COKSS-PADREAAA VLQAGFFLLGGGDPRVRGLYFPA (SEQ ID NO:66)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 83% pure through HPLC.

21. Solid-Phase Chemical Synthesis of $CH_3(CH_2)_{16}$COKSS-PADRESSS FLLTRILTIGGGDPRVRGLYFPA (SEQ ID NO:67)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 80% pure through HPLC.

22. Solid-Phase Chemical Synthesis of $CH_3(CH_2)_{16}$COKSS-PADREAAA FLGGTPVCLGGGDPRVRGLYFPA (SEQ ID NO:68)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 74% pure through HPLC.

23. Solid-Phase Chemical Synthesis of $CH_3(CH_2)_{14}$COKSSQYIKANSKFIG ITEAAAGLSPTVWLSVGGGD-PRVRGLYFPA (SEQ ID NO:69)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 78% pure through HPLC.

24. Solid-Phase Chemical Synthesis of $CH_3(CH_2)_{14}$COKSSQYIKANSK FIGITEAAASIVSPFIPLLGGGD-PRVRGLYFPA (SEQ ID NO:5)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 79% pure through HPLC.

25. Solid-Phase Chemical Synthesis of $CH_3(CH_2)_{16}$COKSS-PADREAAA STLPETTVVRRGGGDPRVRGLYFPA (SEQ ID NO:70)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 82% pure through HPLC.

26. Solid-Phase Chemical Synthesis of $CH_3(CH_2)_{14}$ COKSSQYIKANSKFI GITEAAAFLPSDFFPSVGGGCT-KPTDGNCT (SEQ ID NO:4)

Fmoc solid-phase chemical synthesis scheme was used. The carboxyl group terminus was immobilized, and the peptide chain was extended from C-terminus to N-terminus. The synthesis was carried out in a polypeptide synthesizer, Applied Biosystems 431A. Fmoc amino acids were used as starting materials, the loading amount being 1 mM. The side chain protections were the same as in Example 3. HMP-resin was used as solid-phase carrier, the loading amount being 0.25 mM. That is to say, the ratio of starting materials/resin was 4:1. The amino acid coupled to the resin (the first amino acid at carboxyl terminus of polypeptide) was activated by symmetrical anhydride activation method, and the other amino acids and palmitic acid were activated by the HOBt/DCC activation method, wherein di-coupling was used, and the coupled fatty acid was not subjected to a deprotection step of removing Fmoc protection group.

Cleavage and deprotection: a mixture solution of TFA, EDT, phenyl methyl thioether, crystalline phenol and ultra-pure water in a certain proportion was used to cleave the peptide from the resin and to cleave the side chain protection groups from amino acids, and then a crude peptide product was obtained by precipitation in ethyl ether and rotatory evaporation. The crude peptide product was determined to be about 85% pure through HPLC.

27. Cleavage of $CH_3(CH_2)_{14}$COKSSQYIKANSKFIG-ITEAAAFLPSDFFP SVGGGCTKPTDGNCT (SEQ ID NO:4) Peptide-Resin A TFA cleaving solution (0.75 g phenol, 0.25 ml dithioglycol, 0.5 ml phenyl methyl thioether, 0.5 ml deionized water, 10.0 ml TFA) was used, which can inhibit the occurrence of side reactions maximally. Firstly, the effects the of concentrations of εPA44 peptide-resin in the cleavage reaction on the isolation and purification of the cleavage solution were studied. The reaction conditions were: the volume of cleavage solution was 1.5 ml, the reaction temperature was 25° C., and the reaction time was 2.0 hours. After the completion of the reaction, the resin was filtered off, and to the obtained filtrate was slowly added 1.0 ml dimethyl sulphoxide (DMSO) in a 20° C. water-bath with in time shaking for heat elimination. 2.0 ml of said sample to size exclusion chromatography (SEC) to isolate and purify εPA44. The conditions for SEC were that: the chromatography system comprised P-6000 pump and AKTAexplorer 100; the column had a diameter of 10 mm, a length of 250 mm, and a packing material of Sephadex LH20; the mobile phase was DMSO; the flow rate was 0.4 ml/min. The εPA44 fractions were collected and analyzed by reversed phase high performance liquid chromatography (RP-HPLC) to measure the purity and content of εPA44 and to calculate "peptide/peptide-resin (%)".

TABLE 3

Effects of the concentration of peptide-resin in the cleavage reaction on isolation and purification of cleaved solution

| Concentration of peptide-resin (mg/ml) | Adding DMSO | Peptide/peptide-resin (%)* |
| --- | --- | --- |
| 26.67 | No precipitate | 28.17 |
| 40.00 | No precipitate | 29.80 |
| 53.33 | Precipitate | 26.03 |

*"Peptide/peptide-resin (%)" indirectly reflects the change of "yield".

The results of Table 3 showed that when the concentration of the εPA44 peptide-resin was relatively high (53.55 mg/ml), precipitate would be formed when DMSO was added to the cleaved solution, and the isolated εPA44 constituted 26.03% of the peptide-resin, i.e., the yield was relatively low. When the concentration of the εPA44 peptide-resin was 40 mg/ml, no precipitate was formed when DMSO was added to the cleaved solution, and the isolated εPA44 constituted 29.80% of the peptide-resin, i.e., the yield was relatively high. Hence, the concentration of εPA44 peptide-resin in the cleavage reaction was determined to be 40 mg/ml.

Using the above method and the determined concentration of εPA44 peptide-resin in the cleavage reaction, the effects of cleavage time on the isolation and purification of the cleaved solution of the peptide-resin were studied.

TABLE 4

Effects of cleavage time on isolation and purification of the cleaved solution of peptide-resin

| Cleavage time (hour) | εPA44 purity (%) | Peptide/peptide-resin (%)* |
| --- | --- | --- |
| 0.5 | 55.44 | 19.90 |
| 1.0 | 64.74 | 29.72 |
| 1.5 | 66.16 | 29.89 |
| 2.0 | 64.92 | 29.80 |

TABLE 4-continued

Effects of cleavage time on isolation and purification
of the cleaved solution of peptide-resin

| Cleavage time (hour) | ePA44 purity (%) | Peptide/peptide-resin (%)* |
|---|---|---|
| 2.5 | 61.80 | 22.75 |
| 3.0 | 60.78 | 20.86 |

*"Peptide/peptide-resin (%)" indirectly reflects the change of "yield".

The results of Table 4 showed that when the cleavage time was within 1 to 2 hours, the purity and yield of ePA44 was high after the cleaved solution of peptide-resin was separated by SEC. Thus, the cleavage time was determined to be 1.5 hours.

28. Preliminary Purification of Cleaved Solution of $CH_3(CH_2)_{16}CO$ KSSPADREA AASTLPETTVVRRGGGD-PRVRGLYFPA (SEQ ID NO:70) Peptide-Resin ePA44 was soluble and stable in DMSO, but poorly soluble and stable in other solutions (see Table 5). Thus, DMSO was used as the mobile phase for SEC.

TABLE 5

Solubility and stability of ePA44 in different solution systems

| Solution system | Solubility (mg/ml) | Stability |
|---|---|---|
| 0.1 mol/L PB (pH 6.8) | 0.01 | — |
| 2% Tween80-0.1 mol/L PB(pH 6.8) | 0.08 | — |
| 50% Acetonitrile-0.1% TFA | 1.67 | Unstable |
| 50% Methanol-0.1% TFA | 1.54 | — |
| 50% Ethanol-10 mmol/L HCl | 2.48 | Unstable |
| 50% Ethanol-10 mmol/L phosphoric acid | 2.43 | Unstable |
| DMSO | 11.7 | Stable* |
| 50% DMSO | 2.53 | — |

*The purity and content of ePA44 did not change after ePA44 was placed at room temperature for 1 month, according to the analysis of RP-HPLC.

Batch production was carried out under the above determined cleavage reaction conditions. 55.0 ml cleaved solution of ePA44 peptide-resin was preliminarily purified by SEC. The conditions for SEC were that: the chromatography system comprised P-6000 pump and AKTA explorer 100; the column had a diameter of 25 mm, a length of 850 mm, and a packing material of Sephadex LH20; the mobile phase was DMSO, the flow rate was 2.0 ml/min. The ePA44 fractions were collected and analyzed by RP-HPLC to measure the purity and content of ePA44 and to calculate "peptide/peptide-resin (%)".

TABLE 6

Preliminary purification of the cleaved solution
of peptide-resin and its reproducibility

| Batch No. | Purity (%) | Peptide/peptide-resin (%)* |
|---|---|---|
| 1 | 52.96 | 47.27 |
| 2 | 50.58 | 47.21 |
| 3 | 55.76 | 46.31 |
| x̄ ± Sx | 53.10 ± 2.59 | 46.93 ± 0.54 |

*"Peptide/peptide-resin (%)" indirectly reflects the change of "yield".

The results were set forth in Table 6 and in the chromatography spectrum. When DMSO was used as the mobile phase in said SEC to preliminarily purify the cleaved solution of the peptide-resin, the collected ePA44 fractions 53.10±2.59% pure and constituted 46.93±0.54% of the peptide-resin, meaning a better preliminary purification effect and reproducibility were achieved.

29. Method for Purification of $CH_3(CH_2)_{14}COKSSQYI$-KANSKFI (SEQ ID NO:69)

ePA44 was further purified by chromatography techniques. The purification effects of gel filtration chromatography, ion exchange chromatography and reversed phase chromatography on ePA44 were compared by collecting ePA44 elution peak fractions and analyzing them by RP-HPLC.

The results showed that the gel filtration chromatography did not result in a further purification; the ion exchange chromatography did not give an obvious elution peak, with serious non-specific absorption being accompanied, and thus could not be used; yet the reversed phase chromatography could be used for further purification, though the cost was relatively high.

TABLE 7

Comparison of purities achieved in different
chromatography purification methods

| Purification methods | Purity (%) |
|---|---|
| Gel filtration chromatography | 78.12 |
| Ion exchange chromatography | — |
| Reversed phase chromatography | 99.18 |

30. The Selection of Packing Material for Reversed Phase Chromatography $CH_3(CH_2)_{16}COKSSPADREAAAFLGGTPVCLGGGD$-PRVRGLYFPA (SEQ ID NO:68) was further purified by reversed phase chromatography with different packing materials, and the elution peak fractions were collected and their purities were analyzed by RP-HPLC.

TABLE 8

Comparison of the purification effects of different packing
materials used in the reversed phase chromatography

| Packing material used in the reversed phase chromatography | Purity (%) |
|---|---|
| Delta Pak C18 | 97.69 |
| SOURCE 30 RPC | 94.26 |
| POROS 50 R2 | 96.24 |
| POROS 50 R1 | 98.73 |

The results were shown in Table 8. The purity of the elution peak fractions was relatively high when the packing material POROS 50 R1 with a relatively weak hydrophobicity was used as the fixed phase in the reversed phase chromatography, indicating that packing materials with a relatively strong hydrophobicity (Delta Pak C18, SOURCE 30 RPC and POROS 50 R2) were not suitable as fixed phase for the purification of the product of the present invention having a relatively strong hydrophobicity in reversed-phase chromatography.

31. Effects of Ionizing Reagents on the Reversed Phase Chromatography of $CH_3(CH_2)_{16}COKSSPADRESSSFLLTRILT$-IGGGDPRVRGLYFPA (SEQ ID NO:67)

The reversed phase chromatography was carried out by using column SR 10/450 POROS 50 R1, and the effects of different mobile phases on purity were compared. The chromatography conditions were that: the chromatography system was AKTA explorer 100; the loading amount of the sample was 2.0 ml; the column had a diameter of 10 mm, a length of 450 mm, the packing material was POROS 50 R1; the column temperature was 25° C.; the mobile phases (A, B) were shown in Tables 6-07; the gradient was 0-100% B, 10

CV (column volume); and the flow rate was 4.0 ml/min. The elution peak fractions of εPA44 were collected and its purity was analyzed by RP-HPLC.

TABLE 9

Effects of ionizing reagents on purity in the reversed phase chromatograph

| mobile phase | | Purity |
|---|---|---|
| A | B | (%) |
| 30% ethanol | 90% ethanol | — |
| 30% ethanol -10 mmol/L NaOH | 90% ethanol -10 mmol/L NaOH | 81.73 |
| 30% ethanol -20 mmol/L HCl | 90% ethanol -20 mmol/L HCl | 98.73 |

Table 9 showed that when no ionizing reagent was added to ethanol solution as mobile phase, no obvious elution peak of the product was observed, while when an ionizing reagent was added, the product was completely eluted. Furthermore, the addition of an acid (HCl) was more advantageous to the purification of the product of the present invention than the addition of a base (NaOH).

32. Determining the Column Temperature in the Reversed Phase Chromatography

Phosphoric acid was used as the ionizing reagent instead of hydrochloric acid (which could avoid the corrosion to stainless steel in the system for large scale production in future), and column SR 10/200 POROS 50 R1 was used to further analysis the effects of column temperature on the purity and yield of $CH_3(CH_2)_{16}$COKSSPADREAAAVLQAGF-FLLGGGDPRVRGLYFPA (SEQ ID NO:66) in the reversed phase chromatography. The chromatography conditions were that: the chromatography system was AKTA explorer 100; the loading amount of the sample EPA44 (10.34 mg/ml) was 0.5 ml; the column had a diameter of 10 mm, a length of 200 mm, with the packing material being POROS 50 R1; the column temperature was shown in Table 6-08; the mobile phase A was 30% ethanol-10 mmol/L phosphoric acid; the mobile phase B was 90% ethanol-10 mmol/L phosphoric acid; the gradient was 0-50% B (5 CV), 50-100% B (0.5 CV), and 100-100% B (0.5 CV); and the flow rate was 4.0 ml/min. The elution peak fractions were collected, the purity and content were analyzed by RP-HPLC, and the yield was calculated.

TABLE 10

Effects of the column temperature on the purity and yield in the reversed phase chromatography

| Column temperature (° C.) | Purity (%) | Yield (%) |
|---|---|---|
| 22 | 95.79 | 6.33 |
| 28 | 96.74 | 40.69 |
| 32 | 97.53 | 46.51 |
| 36 | 97.71 | 45.98 |
| 40 | 97.61 | 35.32 |

The results in Table 10 showed that, since the compound of the present invention in the sample was soluble in DMSO, the viscosity of the sample solution was relatively high when the column temperature was 22° C., which was disadvantageous to the diffusion and the binding of the product to the fixed phase, so most of the compound passed through the column, resulting in a relatively low yield of the product after the purification; however, when the column temperature was elevated to 28-40° C., the yield increased significantly than that at room temperature (22° C.). Thus the optimal column temperature in the reversed phase chromatography was 32-36° C.

33. Determining the Loading Amount and the Capacity in the Reversed Phase Chromatography of $CH_3(CH_2)_{14}$COKSSP-DAREAAASILSKTGDPVGGGDPRVRGLYFPA (SEQ ID NO:65)

Since the compound of this example was dissolved in DMSO, the loading amount and the concentration of the present compound in the sample might be important parameters which would affect the chromatography process. Thus, the effects of the loading amount and the capacity on purity and yield of the present compound in the reversed phase chromatography were further studied. The chromatography conditions were that: the chromatography system was AKTA explorer 100; the loading amount of the present compound. (10.34 mg/ml) was shown in Table 6-09; the column had a diameter of 10 mm, a length of 450 mm, with the packing material being POROS 50 R1; the column temperature was 34° C.; the mobile phase A was 30% ethanol-10 mmol/L phosphoric acid; the mobile phase B was 90% ethanol-10 mmol/L phosphoric acid; the gradient was 0-50% B (5 CV), 50-100% B (0.5 CV), and 100-100% B (0.5 CV); and the flow rate was 4.0 ml/min. The elution peak fractions of the present compound were collected, its purity and content was analyzed by RP-HPLC, and the yield was calculated.

TABLE 11

Effects of the loading amount on the purity and yield of the present compound in the reversed phase chromatography

| Loading amount (ml) | Loading amount/column volume (%) | Capacity (mg/ml) | Purity (%) | Yield (%) |
|---|---|---|---|---|
| 0.50 | 1.41 | 0.14 | 99.37 | 68.96 |
| 0.75 | 2.12 | 0.22 | 99.08 | 68.24 |
| 1.00 | 2.83 | 0.29 | 97.88 | 65.66 |

The results in Table 11 showed that when the loading amount was less than 0.75 ml, the purity of the present compound after purification was above 99%, and the yield was near 70%; while when the loading amount was 1.00 ml, the yield decreased and the purity was merely 97.88%, which could not meet the requirements of further purification. Thus, the loading amount and the capacity would generally be about 2% of the column volume and about 0.2 mg/ml.

34. Effects of the Purification of the Stock Solution of $CH_3(CH_2)_{14}$COKSSYIKANSKFIGITEAAAMQWN-STALHQALQDPGGGDPRVRGLYFPA (SEQ ID NO:72) in Batches and its Reproducibility.

Chromatography column AP5 20/275 POROS 50 R1 was used in the batch production. After peptide-resin was cleaved and preliminarily purified, the collected εPA44 sample was divided into 7 parts for high purification, and the effects and reproducibility for batch purification of εPA44 stock solution were furthered studied. The chromatography conditions were that: the chromatography system was AKTA explorer 100; the loading amount of samples (shown in Table 6-10) was 11.0 ml; the column had a diameter of 50 mm, a length of 275 mm, the packing material being POROS 50 R1; the column temperature was 34° C.; the mobile phase A was 30% ethanol-10 mmol/L phosphoric acid; the mobile phase B was 90% ethanol-10 mmol/L phosphoric acid; the gradient was 0-50% B (5 CV), 50-100% B (0.5 CV), and 100-100% B (0.5 CV); and the flow rate was 100.0 ml/min. The collected elution peak fractions of εPA44 were pooled and mixed homogenously, aliquots were removed for analysis. If the sample met the set standards, it was used as the stock solution and was stored at −20° C. until use. The output, yield and specific activity of the product were calculated based on the measured data.

TABLE 12

Effects of batch purification of the raw liquor of the product and is reproducibility

| Sample | | | | ϵPA44 | | | |
|---|---|---|---|---|---|---|---|
| Batch No. | Purity (%) | Concentration (mg/ml) | Times | Output (mg) | Purity (%) | Yield (%) | Specific activity (U/mg) |
| 1 | 52.96 | 10.52 | 7 | 707.00 | 98.54 | 87.28 | 13261.42 |
| 2 | 50.58 | 10.44 | 7 | 695.97 | 98.63 | 86.58 | 11542.77 |
| 3 | 55.76 | 10.21 | 7 | 681.66 | 98.81 | 86.71 | 10265.08 |
| $\bar{x} \pm Sx$ | 53.10 ± 2.59 | 10.39 ± 0.16 | — | 694.88 ± 12.71 | 98.66 ± 0.14 | 86.89 ± 0.43 | 11689.76 ± 1503.57 |

The results were shown in Table 12. After the batch-purified stock solution was highly purified via reversed phase chromatography, the present compound had an output of 694.88±12.71 mg, a purity of 98.66±0.14%, a yield of 86.89±0.43%, and a specific activity of 11689.76±1503.57 U/mg, suggesting a better purification effect and reproducibility.

35. Protocol for Preparing Lyophilized Liposome Injection Formulation of $CH_3(CH_2)_{14}$COKSSQYIKANSKFIGITEAAAPLGFFPDHGGGDPRVRGLYFPA (SEQ ID NO:65)

TABLE 13-continued

Names and volume ratios of the stuffs during the process

| name of the Stuff | Volume ratio |
|---|---|
| Water for injection | 50 |
| Liposome concentrate solution | 2~6 |
| semi-finished product solution for subpackage | 4~8 |

39. A formulation of Caccine for Treatment of Hepatitis B common soybean phospholipid and cholesterol were used to 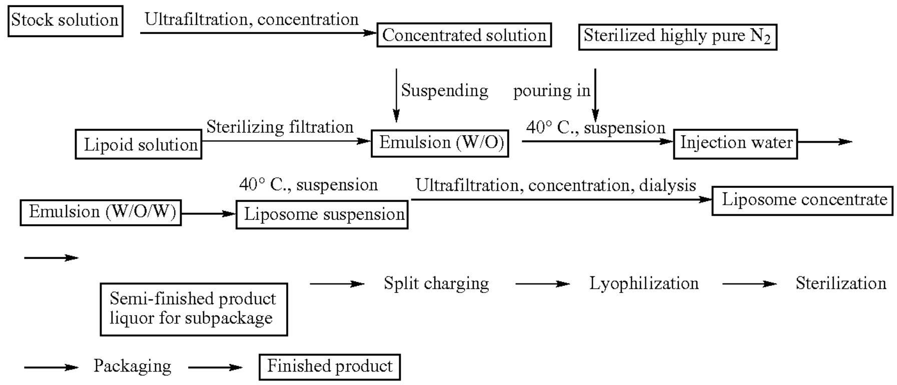 38. Process for Preparing Lyophilized Liposome Injection Formulation of $CH_3(CH_2)_{14}$COKS SQYIKANSKFIGITEAAAYVNTNMGLKGGGDPRVRGLYFPA (SEQ ID NO:62)

Sterile highly pure nitrogen was fed in the process to prevent the oxidization of phospholipids and to promote the volatilization of ethyl ether. The liposome suspension was concentrated and dialyzed repetitively via an ultrafiltration method, so that the concentration and dialysis of the product were 8 folds and above 200 folds respectively, and the residual organic solvents were removed from the solution. The stuffs and their changes in volume during the process were showed in Table 16-1.

TABLE 13

Names and volume ratios of the stuffs during the process

| name of the Stuff | Volume ratio |
|---|---|
| Concentrate solution of the present compound | 1 |
| (Ethyl ether) solution of lipoids | 1 |
| Emulsion (W/O) | 2 | form phospholipid bilayer membrane, wherein the former was the main lipid component, and the latter could also function to stabilize phospholipid bilayer membrane. In addition, a small quantity of palmitic acid and vitamin E were added, wherein the former was capable of increasing the number of negative charges being carried and enhancing the binding of liposome to $CH_3(CH_2)_{14}$CO KSSQYIKANSKFIGITEAAAFLPSDFFPSVGGGDPRVRGLYFPA (SEQ ID NO:1) (pI 8.1), while the latter was used to prevent the oxidization and decomposition of phospholipids. Mannitol and human serum albumin could be used as protection agent and excipients for the lyophilized liposome. Phosphate buffer (pH 6.5) could be used to delay the lysis of soybean phospholipid and to regulate the osmotic pressure to isosmotic state.

40. Determining the Lipid Components in the Vaccine Formulation of $CH_3(CH_2)_{14}$COKSSQYIKANSKFIGITEGGGFLPSDFFPSVSSSDPRVRGLYFPA (SEQ ID NO:61) for Treatment of Diseases and the Conditions for Forming Liposome Liposome was prepared by a double emulsion method. The lipid components were dissolved in ethyl ether solution, mixed with the concentrate of the present compound to form an emulsion (W/O), then poured into phosphate buffer (PB)

or water under a controlled temperature and stirred to form a further emulsion (W/O/W), and liposome was gradually formed as ethyl ether gradually volatilized. The product in free form and aggregate and precipitate in the liquid was removed by concentration in ultrafiltration apparatus and dialysis (the dialysis must be 200 folds or higher) and by filtration via a 10 μm microporous filter. Aliquots were removed for reversed phase high performance liquid chromatography (RP-HPLC) to determine the encapsulation amount, and the encapsulation rate was calculated by comparing to the incorporated amount. $L_9(3^4)$ orthogonal table was used in the experimental design.

TABLE 14

Effects of the ethyl ether solution and the liposome forming conditions on encapsulation rate

| No. | Soybean phospholipid/cholesterol A (mmol/L) | Palmitic acid B (mmol/L) | Temperature C (° C.) | PB concentration D (mmol/L) | Encapsulation rate (%) |
|---|---|---|---|---|---|
| 1 | 40/40 | 0 | 40 | 0 | 93.16 |
| 2 | 40/40 | 2 | 50 | 15 | 54.75 |
| 3 | 40/40 | 6 | 60 | 75 | 44.92 |
| 4 | 60/20 | 0 | 50 | 75 | 69.48 |
| 5 | 60/20 | 2 | 60 | 0 | 97.27 |
| 6 | 60/20 | 6 | 40 | 15 | 79.26 |
| 7 | 80/0 | 0 | 60 | 15 | 53.75 |
| 8 | 80/0 | 2 | 40 | 75 | 79.29 |
| 9 | 80/0 | 6 | 50 | 0 | 109.4 |
| I ↑ | 192.83 | 216.39 | 251.71 | 299.83 | DI the effect |
| II ↓ | 246.01 | 231.31 | 233.63 | 187.76 | CI decrease |
| III | 242.44 | 233.58 | 195.94 | 193.69 | AII gradually |
| R | 53.18 | 17.19 | 55.77 | 112.07 | BIII |
| P< | 0.10 | — | 0.10 | 0.05 | |

Note:
all ethyl ether solutions of Nos. 1–9 contained 6 mmol/L vitamin E.

The results in Table 14 indicated that the main influencing factors were D, C, A and B in order, and the optimal combination of the factor and level was AII BIII CI DI.

41. Effects of the Concentration of the Immunogen on the Encapsulation Rate of the Liposome Based on the formulation and conditions determined by said orthogonal test, the effects of the concentration of the immunogen solution on the encapsulation rate of the liposome were compared.

The results in the following table indicated that when the concentration of the immunogen was 1.0-2.0 mg/ml, the encapsulation rate of the liposome was greater than 90% (P>0.05); while when the concentration was increased to 2.5 mg/ml, the encapsulation rate decreased to below 80% (P<0.001). Thus, the stock solution of the immunogen was concentrated to 1.5-2.0 mg/ml by ultrafiltration during the preparation of the liposome.

TABLE 15

Effects of different concentrations of εPA44 solutions on the encapsulation rate of the liposome

| concentration of εPA44 (mg/ml) | Encapsulation rate of the liposome (%) | | | |
|---|---|---|---|---|
| | 1 | 2 | 3 | $\bar{x} \pm Sx$ |
| 1.0 | 92.12 | 92.80 | 93.62 | 92.85 ± 0.75 |
| 1.5 | 94.38 | 92.67 | 93.96 | 93.67 ± 0.89 |
| 2.0 | 92.94 | 91.93 | 90.70 | 91.86 ± 1.12 |
| 2.5 | 79.94 | 79.30 | 75.23 | 78.16 ± 2.55 |

42. Determining the Formulation of a Lyophilized .epsilon.PA44 Liposome Injection of $CH_3(CH_2)_{16}COKSSQYI$-KANSKFIGITEAAAFLPSDFFPSVGGGDPRVRGLYFPA (SEQ ID NO:74)

In the Table 16, all of the formulations 1-11 contained a buffer of 5% mannitol/10 mmol/L phosphate($KH_2PO_4$/$Na_2HPO_4$ was 60/40)

TABLE 16

Effects of concentrated liposome solution, excipients and concentrations thereof on lyophilization

| No. | liposome Concentrate * (%, V/V) | Excipients and concentrations thereof (%, W/V) | degree of size shrinkage of the liposome after lyophilization |
|---|---|---|---|
| 1 | 50 | — | ++++ |
| 2 | 25 | — | +++ |
| 3 | 50 | Polyvidone K30(1.0) | +++ |
| 4 | 25 | Polyvidone K30(1.0) | ++ |
| 5 | 50 | Polyvidone K30(0.5) | +++ |
| 6 | 25 | Polyvidone K30(0.5) | +++ |
| 7 | 50 | Human serum albumin (1.0) | − |
| 8 | 25 | Human serum albumin (1.0) | − |
| 9 | 50 | Human serum albumin (0.5) | + |

TABLE 16-continued

Effects of concentrated liposome solution, excipients
and concentrations thereof on lyophilization

| No. | liposome Concentrate * (%, V/V) | Excipients and concentrations thereof (%, W/V) | degree of size shrinkage of the liposome after lyophilization |
|---|---|---|---|
| 10 | 25 | Human serum albumin (0.5) | + |
| 11 | — | — | − |

* Note:
the volume of the concentrated liposome solution was equal to the volume of the emulsion (W/O) (see also Table 16-1).

When the addition amount of the concentrated liposome solution was 25-50% (v/v) of the semifinished product liquor for subpackage, addition of 1% human serum albumin as excipient will result in better lyophilization effects. Thus, when the volume of the concentrated liposome solution was equal to the volume of the emulsion (W/O), the volume of the concentrated liposome solution was determined as 37.5% (v/v) of the volume of the product liquor for for subpackage, i.e., an average level of the amount of the concentrated liposome solution. In this case, the concentrations of the adjuvants in the product liquor for subpackage should meet the requirements as set forth in Table 16-4. The volume of subpackage should be 1 ml and meet the requirements for the formulation of lyophilized liposome injection. In practice, the volume of the concentrated liposome solution usually is greater than the volume of emulsion (W/O), so the volume of the product liquor for subpackage may be increased. Thus, the actual subpackage volume is calculated according to the following formula.

$$\frac{\text{Subpackage\_Volume}}{\text{Volume\_of\_Emulsion}(W/O)} \times 37.5\% (ml)$$

1 ml water is added to form a suspension for administration.

43. Results of Batch Production of Lyophilized Injection Formulation of $CH_3(CH_2)_{16}$COKSSQYIKANSKFIG-ITEAAAYVNTNMGGGGDPRVRGLYFPA (SEQ ID NO:60) and its Reproducibility Under the process conditions as determined above, the batch production of the lyophilized injection formulation of the product was carried out by ultrafiltrating and concentrating the stock solution, preparing liposome, adding adjuvants, subpackaging, lyophilizing, and radiation sterilizing.

tively; the content of ϵPA44 was 303.11±7.47 µg/bottle; the specific activity was 13627.46±648.95 U/mg. Thus, a good reproducibility was achieved.

44. Transformation Experiment of Lymphocytes with $CH_3(CH_2)_{16}$COKSS PADREAAALLPIFFCLWVGGGDPRVR-GLYFPA (SEQ ID NO:59)

Balb/c mice of 2-3 months old (both male and female) were divided into 8 groups, and were immunized with ϵPA30 at both postpede palmas once a week for three times at different doses: 0.001 nmol, 0.01 nmol, 0.1 nmol, 0.5 nmol, 1 nmol, 10 nmol, 20 nmol, 40 nmol respectively. The mice were decapitated, their both popliteal lymph nodes were enucleated aseptically and were tested by the 3H-TdR incorporation method. The results proved that ϵPA30 was effective from 0.01 nmol, and the effect was dose dependent within the dose range from 0.01 nmol to 20 nmol.

45. Identification of Neutralizing Antibodies of $CH_3(CH_2)_{14}$COKSSPADRE AAAGLSPTVWLSVGGGDPRVRGLY-FPA (SEQ ID NO:58) and Specificity Determination Balb/c mice of 2-3 Months old (both male and female) were divided into 8 groups and 40 nmol, and were immunized with ϵPA44 at both postpede palmas once a week for three times at different doses: 0.001 nmol, 0.01 nmol, 0.1 nmol, 0.5 nmol, 1 nmol, 10 nmol, 20 nmol respectively, 3 weeks after the immunization, the mice were bled by removing their eyeballs and serums were collected. Antibodies were tested by the double-antibody-sandwich method. The specificity was tested by antibody competitive inhibition test using of the 10 world wide available monoclonal antibodies. The results proved that ϵPA44 induced the generation of antibody at 0.01 nmol, and the induction was dose dependent within the dose range from 0.01 nmol to 20 nmol. These antibodies were HBV neutralizing antibodies.

46. Test of Inducing Th1 Activation with $CH_3(CH_2)_{14}$COKSS PADREGGGLLVPFVQWFVSSSDPRVRGLYFPA (SEQ ID NO:57)

Balb/c mice (both male and female) of 2-3 Months old were divided into 8 groups, and were immunized with ϵPA44 at both postpede palmas once a week for three times at different doses: 0.001 nmol, 0.01 nmol, 0.1 nmol, 0.5 nmol, 1 nmol, 10 nmol, 20 nmol, and 40 nmol respectively. 3 weeks after immunization, the mice were bled by removing their eyeballs and serums were collected. Th1/Th2 cytokines were

TABLE 17

Results of batch production of lyophilized injection formulation
of the present compound and its reproducibility

| Batch No. | Encapsulation rate of liposome (%) | Distribution of the particle size of liposome (µm)* | | | content of EPA44 (µg/bottle) | Specific activity (U/mg) |
|---|---|---|---|---|---|---|
| | | D50 | D90 | D99 | | |
| 1 | 90.08 | 0.25 | 0.72 | 2.74 | 294.76 | 14173.51 |
| 2 | 88.38 | 0.30 | 0.75 | 2.06 | 309.14 | 13798.85 |
| 3 | 90.83 | 0.33 | 0.94 | 3.69 | 305.43 | 12910.01 |
| x̄ ± Sx | 89.76 ± 1.26 | 0.29 ± 0.04 | 0.80 ± 0.12 | 2.83 ± 0.82 | 303.11 ± 7.47 | 13627.46 ± 648.95 |

*Note:
D50, D90 and D99 represented that 10%, 50% and 90% particles were smaller than the identified size value respectively.

The results of Table 17 showed that the encapsulation rate of the liposome in the batch production was 89.76±1.26%. For the injection formulation, the D50, D90 and D99 of the liposome were 0.29±0.04, 0.80±0.12 and 2.83±0.82 respectested by ELISA. The results proved that ϵPA44 induced the generation of IFN-γ and IL-2 at the dose of 0.01 nmol, and the induction was dose dependent within the dose range from 0.01 nmol to 10 nmol.

47. Using the ELISPOT Method to Test the Cytotoxicity Induced by $CH_3(CH_2)_{14}COKSSPADREAAAFLPSDFFPSVGGGDPRVRGLYFPA$ (SEQ ID NO:56)

Balb/c mice of 2-3 Months old (both male and female) were divided into 8 groups, and were immunized with the present compound at both postpede palmas once a week for three times at different doses: 0.001 nmol, 0.01 nmol, 0.1 nmol, 0.5 nmol, 1 nmol, 10 nmol, 20 nmol, and 40 nmol respectively. Bloods were taken postorbitally from mice under sterile conditions on the $6^{th}$, $12^{th}$, $18^{th}$ and $24^{th}$ day after the end of immunization respectively and were anticoagulatant-treated. PBMCs were isolated by Ficoll-Hypaque method, and were cultured in RPMI1640 culture media (containing 10% calf serum, and 100μ/ml penicillin-streptomycin) ($10^6$/ml, 96-well culture plate) in vitro for one day. After they returned to the original growth state, they were used as test cells. ELISPOT 96-well cell culture plate was pre-coated with IFN-γ coating antibody overnight, each well was treated in triplicate. The wells were blocked with RPMI1640 containing 5% calf serum at room temperature for 1 hour. After drying in air, test cells were added ($5 \times 10^4$ cells/100 μl/well, containing RPMI1640 media, 10% calf serum, 100μ/ml myciline, and 1 μg/ml peptide), wherein the PBMC of mice immunized with melan A27-35 peptide were set as negative control. After being cultured for 15 hours, the plate was washed for 6 times and dried in air, the test antibody labelled with biotin was added and incubated at 37° C. for 1 hour. Then the plate was washed again and dried in air, the substrate was added for visualization and the number of spots was counted. The results indicated that the minimum effective dose for the present compound is 0.01 nmol, and the effect was dose dependent within the dose range from 0.01 nmol to 20 nmol.

48. Test of $CH_3(CH_2)_{14}COKSSQYIKANSKFIGITEAAAFLPSDF$ FPSVGGGDPRVRGLYFPA (SEQ ID NO: 1) for Inducing Proliferation of Human Peripheral Blood Mononuclear Cells (PBMCs)

Anticoagulant peripheral blood was collected from normal persons under sterile conditions, PBMCs were isolated by conventional Ficoll-Hypaque density gradient centrifugation and were cultured in RPMI1640 culture media (containing 10% calf serum, 100 u/ml penicillin-streptomycin, L-glutamine) in vitro on 24-well culture plates at the cell concentration of $10^6$/ml. Blank control group, test group and Pre-S(2) control group were included, to which IL-2 (30 IU/ml) and test drug (0.1 μg/ml, 1 μg/ml, 10 μg/ml) were added. After the cells were cultured for 6 days, IL-2 and the test drug were added at the same dose to stimulate the cells again, and then 3H-TdR (1 uCi/ml) was added. After the cells were further cultured for 18 hours, they were collected and tested by liquid scintillation. The results indicated that the present compound stimulated the proliferation of human PBMCs in a manner of dose dependence within the dose range of 0.1 μg, 1 μg and 10 μg/ml.

49. Induction of Th1/Th2 Activation of Peripheral Blood Mononuclear Cells (PBMCs) from Healthy Human by $CH_3CH_2CH=CHCH_2CH=CH(CH_2)CH=CH(CH_2)_7$ COKSSPADREGGGWLSLLVPFVSSSDPR VRGLYFPA (SEQ ID NO:55).

Anticoagulant peripheral blood was collected from healthy person under sterile conditions, PBMCs were isolated by conventional Ficoll-Hypaque density gradient centrifugation and were cultured in RPMI1640 culture media (containing 10% calf serum, 100 u/ml penicillin-streptomycin, L-glutamine) in vitro on 24-well culture plates at the cell concentration of $10^6$/ml. Normal control group and test drug group were included, to which IL-2 (30 IU/ml) and test drug (0.1 μg/ml, 1 μg/ml) were separately added. After the cells were cultured for 6 days, the test drug was added at the same dose to stimulate the cells again. After 3 days, the supernatant was collected by centrifugation, and the Th1/Th2 diffentiation was tested by Endogen kit. The results indicated that Pre-S (2) could induce strong conversion of T-cell into Th2 type, but can rarely induce the conversion of T-lymphocytes into Th2 type; while the test drug was able to induce the conversion of T-lymphocytes into both Th1 and Th2 types, predominantly Th1 type.

50. HBV-Specific CTL Induced by $CH_3CH_2CCH=CHCH_2CH=CH(CH_2)CH=CH(CH_2)_7$ COFLPSDFFPSVAAADPRVRGLYFPA (SEQ ID NO:54) and Cytotoxicity Test Human PBMCs were divided into groups and cultured in RPMI1640 culture media (containing 10% calf serum, and 100μ/ml penicillin-streptomycin) ($10^6$/ml, 24-well culture plates) in vitro for one day. After they recovered the original growth state, IL-2(30-IU/ml) and test drug (0.1 μg/ml, 1 μg/ml) were separately added. The cells were further cultured for 6 days, then they were stimulated with IL-2 and the test drug at the same doses once a week for 3 times. 3 days after the last stimulation, antigen-specific effective CTL cells were obtained. Cytotoxicity was tested by standard $^{51}Cr$ release tests and compared. Target cells (T2 cells and HepG2.2.1.5 cells pre-coated with peptide) were grown to a good state. 10 hours before the cells were used, 10 μg/ml test drug was added to the culture, and the cells were incubated. $10^6$ Target cells were placed in 1 ml RPMI1640 media (containing 20% calf serum), and 100 μCi $^{51}Cr$ (NEN) was added for labelling in water-bath at 37° C. for 2 hours. The labelled target cells were washed with sterilized PBS buffer for 3 times under centrifugation (500 rpm/5 min), and were plated on 96-well V-bottom culture plates in an amount of $10^4$ target cells/50 μl/well, each well was treated in triplicate. Effector cells were separately added at an effector cell/target cell ratio (E/T) of 12.5:1, 25:1, 50:1 and 100:1, gently shaken to uniformity, centrifuged for 3-5 minutes at 500 rpm, and co-cultured at 37° C. for 4 hours in a 5% $CO_2$ incubator. γ-count values of supernatants were measured, wherein maximum release value was the γ-count value of the supernatant obtained by culturing $10^4$ target cells in a 1 mol/L hydrochloric acid, and the minimum release value was the γ-count value of the supernatant obtained by culturing $10^4$ target cells in a RPMI1640 media containing 20% calf serum. The minimum release value was 30% lower than the maximum release value. The formula for calculating $^{51}Cr$ release percentage was: $[(CPM_{sample} - CPM_{minimum\ release})/(CPM_{maximum\ release} - CMP_{minimum\ release})] \times 100\%$.

The results of $^{51}Cr$ release test indicated that, after culturing human PBMCs in vitro, repetitively stimulating to generate antigen-specific CTL cells and amplifying them in number, and cytotoxically killing HepG2.2.15 cells, peptide antigen pre-coated T2 cells and E6 cells, all T-lymphocytes induced by the test drug were able to specifically kill peptide pre-coated T2 cells, E cells and HepG2.2.15 cells, and the target cell-specific lysis rate was up to 62.8%.

51. Using ELISPOT Method to Test the Cytotoxicity of $CH_3(CH_2)_7CH=CH(CH_2)CO$, $CH_3CH_2CH=CHCH_{22}CH=CH(CH_2)_7CO_7KSSQYIK-ANSKFIGITEGGGDPRVRGLY$ (SEQ ID NO:73)

After being firstly stimulated for 6 days, human PBMCs were used as tested cells. ELISPOT 96-well cell culture plate was pre-coated with IFN-γ coating antibody and stayed overnight, each well was repeated in triplicate. Then the wells were blocked with RPMI1640 containing 5% calf serum at room temperature for 1 hour. After drying in air, the test cells were added ($5 \times 10^4$ cells/100 μl/well, containing RPMI1640 media, 10% calf serum, 100μ/ml myciline, and 1 μg/ml peptide). Normal PBMCs that were not stimulated were included as negative control. After being cultured for 15 hours, the plate was washed for 6 times and dried in air, the test antibody labeled with biotin was added and incubated at 37° C. for 1 hour. Then the plate was washed again and dried in air, and the substrate was added for visualization and the number of spots was counted under an inverted microscope. The results indicated that the present compound, induced cytotoxicity in a manner of dose dependence within the dose range from 0.01 nmol to 20 nmol.

52. Test of HBV Antigen Inhibition Induced by $CH_3(CH_2)_{16}$CO KSSPADREAAALLDYQGMLPVGGGD-PRVRGLYFPA (SEQ ID NO:52)

HepG2.2.1.5 cell monolayer was cultured on a 24-well culture plate, PBMCs activated by setrile drugs at seven different concentrations which were two-fold serial dilution were added at an effector/target ratio of 10:1. Normal control and drug control were included simultaneously. Supernatants were collected on the $3^{rd}$, $5^{th}$, $7^{th}$, $10^{th}$ and $14^{th}$ days of the culturing and the levels of HBsAg and HBeAg were measured. The results showed that the present compound inhibited the concentration of HBsAg and HBeAg in a manner of dose dependence within the dose range from 0.01 nmol to 20 nmol.

53. Test of Inducing Proliferation of Lymphocytes in PBMC of Acute Hepatitis B Patient with $CH_3(CH_2)_{14}$COKSSQYI-KANSKFIGITEAAALLCLIFLLVGGGDPRVRGLYFPA (SEQ ID NO:51)

Anticoagulant peripheral blood was collected aseptically from acute hepatitis B patient in convalescent phase, PBMCs were isolated by conventional Ficoll-Hypaque density gradient centrifugation and were cultured in RPMI1640 cultural media (containing 10% calf serum, 100 u/ml penicillin-streptomycin, L-glutamine) in vitro on 24-well cell culture plate at a concentration of $10^6$/ml. Blank control group, test group, and Pre-S (2) control group were included. IL-2 (30 IU/ml) and test drug (0.1 μg/ml, 1 μg/ml, 10 μg/ml) were separately added into the wells. After the cells were cultured for 6 days, IL-2 and the test drug were added at the same doses to stimulate the cells again. Then 3H-TdR (1 uCi/ml) was added and further cultured for 18 hours. The cells were collected and tested by liquid scintillation. The results indicated that the present compound stimulated the proliferation of PBMCs from acute hepatitis B patient in convalescent phase in a manner of dose dependence within the dose range of 0.1 μg, 1 μg and 10 μg/ml.

54. Analysis of the Lymphocyte Activation of PBMCs from Hepatitis B Patient Induced by $CH_3(CH_2)_{10}$COKSSPA-DREGGGSLNFLGGTTVSSSDPRVRGLYFPA (SEQ ID NO:50).

Acute and chronic hepatitis blank control groups, acute hepatitis+/test drug group and chronic hepatitis+/test drug group were included to test the Th1/Th2 activation by Endogen kit or EELISPOT method. Results: the concentrations of cytokines such as IL-4, IL-10, IFN-γ, etc. in the culture supernatants of PBMCs from patients measured by ELISA method and changes thereof indicated that, Pre-S (2) induced stronger T-cell conversion into Th2 type, but did not induce substantially the T-lymphocytes conversion into Th1 type; while the test drug was able to induce the conversion of T-lymphocytes into both Th1 and Th2 types, with the conversion into Th1 type the most obvious.

55. $CH_3(CH_2)_{14}$COKSSQYIKANSKFIGITEAAAFLPSD-FFPSVGGGDPRVRGLYFPA (SEQ ID NO:1) Induced the Generation of HBV-Specific Effective CTL From Hepatitis Patients' PBMC and the Cytotoxicity was Tested.

Acute and chronic hepatitis blank control groups, acute hepatitis+test drug group and chronic hepatitis+test drug group were included. The PBMC's from the patients were cultured in vitro and stimulated repetitively to generate antigen-specific effective CTL cells and amplified their number. Then they were used to cytotoxically kill peptide antigen pre-coated T2 cells, E6 cells, and HepG2.2.15 cells. The results indicated that all T-lymphocytes induced by the test drug were able to specifically kill aforesaid three target cell lines; as to PBMCs from acute hepatitis patient in convalescent phase, the target cell-specific lysis rate was up to 68.6%; while as to PBMCs from chronic hepatitis patient, the target cell-specific lysis rate was a little lower, but was still up to 42.6%;

56. Using ELISPOT Method to Test Cytotoxicity of $CH_3(CH_2)_{14}$COKSS QYIKANSKFIGITEAAAFLPSDFFPS-VGGGDPRVRGLYFPA (SEQ ID NO:1) in Hepatitis B Patient After being firstly stimulated for 6 days, human PBMCs were used as test cells. ELISPOT 96-well cell culture plate was pre-coated with IFN-γ coating antibody and stayed overnight. Each well was treated in triplicate. The wells were blocked with RPMI1640 containing 5% calf serum at room temperature for I hour. After dried in air, the test cells were added ($5 \times 10^4$ cells/100 μl/well, containing RPMI1640 media, 10% calf serum, 100μ/ml penicillin-streptomycin, and 1 μg/ml peptide). Unstimulated normal PBMCs were included as negative control. After the cells were cultured for 15 hours, the plate was washed for 6 times and dried in air. Then the test antibody labeled with biotin was added and incubated at 37° C. for 1 hour. The plate was washed again and dried in air, and the substrate was added for development. The number of spots was counted under an inverted microscope. The results indicated that εPA30 induced cytotoxicity in a manner of dose dependence within the dose range from 0.01 nmol to 20 nmol.

57. $CH_3(CH_2)_{14}$COKSSQYIKANSKFIGITEAAAFLPSD-FFPSVGGGDPRVRGLYFPA (SEQ ID NO:1) Induced Th1 Activation in HBV Transgenic Mice HBV-DNA transgenic mice (ayw type Kunming species mice transfected with the full genome of HBV (1.3 Kb) were used. They were grouped randomly, 10 mice per group. The mice were administered respectively with 3 doses, 10, 100 and 1000 U/mouse, subcutaneously below both costal regions and at both postpede palmas. The immunizations were enhanced once a week for 3 times. INF-α2b (15000 U/mouse) was included as positive control, and physiological saline was included as negative control. Before administration, on the $10^{th}$, $20^{th}$ and $30^{th}$ day after the end of administration. On the $30^{th}$ day after the end of administration, spleens were removed from mice, lymphocytes were separated therefrom and were stimulated with test drug at a concentration of 10 ng/ml in vitro for 3 days. Then supernatants were collected and the secretion levels of cytokines such as TNF-α, IFN-γ, IL-4, etc. in supernatants were measured by ELISA, and the activity of the test drug for inducing the conversion of Th1/Th2 type from T cells in subjects was analyzed. The results showed that the secretion of IFN-γ was stronger, and no obvious dose-effect dependence relation was observed for IL-4.

58. $CH_3(CH_2)_{14}$COKSSQYIKANSKFIGITEAAAFLPSD-FFPSVGGGDPRVRGLYFPA (SEQ ID NO:1) Induced CTL Activity in HBV Transgenic Mice HBV-DNA transgenic mice (ayw type Kunming species mice transfected with the full gene of HBV (1.3 Kb) were used. They were grouped randomly, with 15 mice per group.

The mice were administered respectively with 3 doses, 10, 100 and 1000 U/mouse, subcutaneously below both costal regions and at both postpede palmas. The immunizations were enhanced once a week for 3 times. INF-α2b (15000 U/mouse) was included as positive control, and physiological saline was included as negative control. Before administration, and on the $10^{th}$, $20^{th}$ and $30^{th}$ day after the end of administration. On the $30^{th}$ day after the end of administration, spleens were removed from the mice, and lymphocytes were isolated therefrom and were stimulated with 10 ng/ml test drug in vitro for 3 days. The expression frequency of IFN-γ secreting cells in peripheral blood lymphocytes was measured by the ELI-SPOT method. The results showed that, on the $30^{th}$ day after the end of immunization, the expression frequency of IFN-γ secreting cells in peripheral blood lymphocytes increased with the increase of the immunization dose, wherein the immunization doses of 100 and 1000 U/mouse resulted in an obvious increase of the expression frequency of IFN-γ secreting cells in peripheral blood lymphocytes in vivo, with the highest of 3660±IFN-γ secreting cells/$10^6$ PBMC being detected.

59. $CH_3(CH_2)_{14}$COKSSQYIKANSKFIGITEAAAFLPSD-FFPSVGGGDPRVRGLYFPA (SEQ ID NO:1) Inhibits Hepatitis B Surface Antigen (HBsAg) in HBV Transgenic Mice HBV-DNA transgenic mice (ayw type Kunming species mice transfected with the full gene of HBV (1.3 Kb) were used. They were grouped randomly, with 15 mice per group. The mice were administered respectively with 3 doses, 10, 100 and 1000 U/mouse, subcutaneously below both costal regions and at both postpede palmas, and the immunizations were enhanced once a week for 3 times. INF-α2b (15000 U/mouse) was included as positive control, and physiological saline was included as negative control. Before administration, and on the $10^{th}$, $20^{th}$ and $30^{th}$ day after the end of administration. On the $10^{th}$, $20^{th}$ and $30^{th}$ after the end of the three immunizations, bloods were taken, serums were separated, and, the contents of the lever of HBsAg in the serums were separately measured by the ELISA method. The results showed that HBsAg in the serum was decreased in a manner of dose-dependence and time-dependence.

60. $CH_3(CH_2)_{14}$COKSSQYIKANSKFIGITEAAAFLPSD-FFPSVGGGDPRVRGLYFPA (SEQ ID NO:1) Inhibits Virus Replication in HBV Transgenic Mice HBV-DNA transgenic mice (ayw type Kunming species mice transfected with the full gene of HBV (1.3 Kb) were used. They were grouped randomly, with 15 mice per group. The mice were administered respectively with 3 doses, 10, 100 and 1000 U/mouse, subcutaneously below both costal regions and at both postpede palmas. The immunizations were enhanced once a week for 3 times. INF-α2b (15000 U/mouse) was included as positive control, and physiological saline was included as negative control. Before administration, and on the $10^{th}$, $20^{th}$ and $30^{th}$ day after the end of administration. On the $10^{th}$, $20^{th}$ and $30^{th}$ after the end of three immunizations, bloods were taken, serums were separated, and the copy numbers of HBV DNA in the serums were separately measured by quantitative PCR method. The results showed that the copy number of HBV DNA was obviously decreased in a manner of dose-dependence and time-dependence.

61. Determining the Isoelectric Point of $CH_3(CH_2)_{14}$COKSSQ YIKANSKFIGITEAAAFLPSDFFPS-VGGGDPRVRGLYFPA (SEQ ID NO:1)

Supported ampholyte pH gradient isoelectric focusing was employed. Pretreatment: 8N urea and 2% TritonX-114. Urea at the corresponding concentration and 0.5% TritonX-114 were also added to polyacrylamide gel. Conventional Coomassie brilliant blue was used for dyeing. The results indicated that the isoelectric point of the present compound was pH 7.2.

62. UV Spectrum Determination of $CH_3(CH_2)_{14}$COKSSQYIKANSKFI GITEAAAFLPSDFFPSVGGGD-PRVRGLYFPA (SEQ ID NO:1)

The semifinished product of ε-PA44, a polypeptide for treatment of hepatitis B, was scanned with UV spectra by a UV spectrophotometer, and the wavelength of the maximum absorption was determined. Samples to be tested were diluted to a concentration measurable for the spectro photometer, and aliquots were taken to be scanned with UV spectra having a wavelength from 190 nm to 500 nm, and 50% ethanol was used as blank control. The results showed that the maximum UV characteristic absorption peak was at 276 nm.

63. Determination the Peptidic Pattern of $CH_3(CH_2)_{14}$COKSSQYIKAN SKFIGITEAAAFLPSDFFPSVGGGD-PRVRGLYFPA (SEQ ID NO:1)

1 mg trypsin was weighed and placed in a 1.5 ml centrifuge tube, and dissolved in 0.1M $NaHCO_3$ at a concentration of 1 mg/ml, forming a trypsin stock solution. 10 μl trypsin solution was added into a sample tube of ε-PA44. The centrifuge tube was covered and the reaction mixture was incubated at 37° C. for 2 hours. When the digestion reaction was being carried out, the residual trypsin solution was placed on ice. After 2 hours, 10 μl trypsin solution was added to the digestion mixture. The centrifuge tube was covered, and incubated at 37° C. for 4.5 hours. After the reaction was complete, 10 μl TFA was added to terminate the reaction. 20 μl aliquot was taken and directly analyzed by RP-HPLC (HP 1100 high performance liquid chromatography; Waters Symmetry $C_{18}$ column having a particle size of 5 μm, a pore size of 100 Å, a column diameter of 3.9 mm, and a column length of 150 mm).

Thus, the characteristic peptidic pattern was obtained.

64. Purity Analysis of $CH_3(CH_2)_{14}$COKSSQYIKANSKFIG-ITEAAAFLPSDF FPSVGGGDPRVRGLYFPA (I) (SEQ ID NO:1)

The purity of εPA44 having a molecular weight of about 4947.37 Dalton was analyzed by a high performance gel chromatography column having an effective molecular weight linear range of from 1,000 to 80,000, wherein the absorption of peptide bond was detected by 214 nm UV light, the percentage purity of the main peak of the product was calculated by area normalization method. The instruments and chromatography conditions were: Waters Delta 600 high performance liquid chromatography; Waters Millennium[32] chromatography software; Waters Ultrahydrogel 250 high resolution gel analyte column (having a particle size of 6 μm, a pore diameter of 250 Å, a column diameter of 7.8 mm, and a column length of 300 mm); mobile phase (40% $CH_3CN$-0.1% TFA, wherein $CH_3CN$ is acetonitrile, HPLC grade, and made in Linhai, Zhejiang, and TFA is trifluoroacetic acid, HPLC grade, and made in Sigma Company, U.S.A.). 2 μl of the concentrated semifinished product was loaded onto the column. The flow rate was 0.5 ml/min. The absorbance was detected at the UV wave length of 214 nm. The results showed that the product was 99.8% pure.

65. Purity Analysis of $CH_3(CH_2)_{14}$COKSSQYIKANSKFIG-ITEAAAFLPSDF FPSVGGGDPRVRGLYFPA (II) (SEQ ID NO:1)

The product was separated by a gradient reversed phase high pressure liquid chromatograph, the absorbance of peptide bond was detected at 214 nm UV light. The percentage purity of the main peak of εPA44 was calculated by area normalization method, The instruments and chromatography conditions were: HP 1100 high performance liquid chromatography; Waters Symmetry $C_{18}$ column (having a particle size of 5 μm, a pore diameter of 100 Å, a column diameter of 3.9 mm, and a column length of 150 mm) and protection column (having a particle size of 5 μm, a pore diameter of 100 Å, a column diameter of 3.9 mm, and a column length of 20 mm); mobile phase A (100% $H_2O$-0.1% TFA) and mobile phase B (100% $CH_3CN$-0.1% TFA) at a linear gradient of 10% B-70% B/30 min wherein $CH_3CN$ was acetonitrile, HPLC grade, and made in Linhai, Zhejiang, and TFA was trifluoroacetic acid, HPLC grade, and made in Sigma Company, U.S.A.; The flow rate was 1.0 ml/min. The absorbance was dectected at the UV wavelength of 214 nm. The results showed that the product was 99.9% pure.

66. Determination of Content of $CH_3(CH_2)_{14}$COKSSQYIKANSKFIGITEAAAFLPSDFFPSVGGGDPRVRGLYFPA (SEQ ID NO:1)

The contents of the product in the fractions, the semifinished product, the concentrate and the concentrated liposome solution were determined by external reference method and reversed phase high performance liquid chromatography (RP-HPLC).

The test samples were diluted to a concentration within the measurable range of the standard curve of the product. Aliquots were sampled and analyzed by RP-HPLC, and the contents of the product in the test samples were calculated according to the equation of linear regression of the established quantitative standard curve, i.e., $Y_{peak\ area}=12.362 X_{concentration}+80.702$, and the dilution factor of the test samples.

The instruments and chromatography conditions were: HP 1100 high performance liquid chromatography; Waters Symmetry $C_{18}$ column (having a particle size of 5 μm, a pore diameter of 100 Å, a column diameter of 3.9 mm, and a column length of 150 mm) and protection column (having a particle size of 5 μm, a pore diameter of 100 Å, a column diameter of 3.9 mm, and a column length of 20 mm); mobile phase A (100% $H_2O$-0.1% TFA) and mobile phase B (100% $CH_3CN$-0.1% TFA) at a linear gradient of 30%-60% B/15 min, wherein $CH_3CN$ was acetonitrile, HPLC grade, and made in Zhejiang Linhai, and TFA was trifluoroacetic acid, HPLC grade, and made in Sigma Company, U.S.A. The flow rate was 1 ml/min. The absorbance was detected at the UV wavelength of 214 nm. The results showed that the content of the product was 4.5 mg/ml.

67. Determination of the Molecular Weight of $CH_3(CH_2)_{14}$COKSSQYIKANSKFI GITEAAAFLPSDFFPSVGGGDPRVRGLYFPA (SEQ ID NO:1)

Electrospray ionization mass spectrometry (ESI-MS) was used to make polypeptides and proteins molecules carry various charges and form different mass charge ratios, so that the molecular weight of εPA44 was accurately determined according to the carried charges obtained by the simultaneous equation of the mass charge ratios two adjacent peaks ($n=m_1-H/M_2-m_1$). Instruments and mass spectra conditions are: PE ABI 2000 mass analyzer; PE SCIEX Analyst 1.0b3 mass spectra analysis software; scanning Q1 positive ion, GAS1: 20 GAS2: 0 CUR: 20 TEM: 50° C. CAD: 0 IS: 5500 NC: 2 DP: 30 FP: 350 EP: −10 DF: 0 1800. The results showed that the molecular weight was 4929.12 u and was consistent with the theoretic value.

68. Determination of Particle Size Distribution of the Liposome of $CH_3(CH_2)_{14}$COKSSQYIKANSKFIGITEAAAFLPSDFFPSVGGGDPRVRGLYFPA (SEQ ID NO:1)

Laser Particle Sizer "Analysette 22" (Germany, FRITSCH) and micro pool (Germany, FRITSCH) were used to determine the particle size distribution of εPA44 liposome. The detection range was from 0.1 μm to 100.25 μm, and the resolution was 62 tract (9 mm/38 mm). The lyophilized εPA44 liposome product was sampled randomly, dissolved in water, diluted, mixed to uniformity, and tested. The results showed that the D50 of the product was 0.25 μm, the D90 was 0.72 μm, and the span was less than 3.

69. Determination of Potency/Specific Activity of the Semifinished Product of $CH_3(CH_2)_{14}$COKSSQYIKANSKFIGITEAAAFLPSDFFPSVGGGDPRVRGLYFPA (SEQ ID NO:1)

The semifinished product to be tested was diluted to a concentration within the measurable range of the potency determination. An enzyme-linked plate(酶联板) was coated, blocked, bound by enzyme-labeled antibody, and developed. The absorbance at 450 nm (A450 nm) was detected by an enzyme-labeling device, and compared to the reference of the product. The potency of εPA44 in the extract of the sample was determined, and the specific activity of the semifinished product (半成品) was calculated.

The reference of the product was 10-fold diluted with 50% ethanol, and then was two-fold serially diluted. 100 μl dilutions were separately added to the wells on the 96-well enzyme-linket immunosorbent assay plate, each well was repeated in triplicate. Coating was carried out in refrigerator at 4° C. for 20-24 hours. The stock solution of εPA44 was diluted and coated similarly to the reference. 100 μl of 50% ethanol was added to negative control wells. After the coating was completed, 200 μl 1% calf serum was added to each well, and blocked in refrigerator at 4° C. for 2 hours. The enzyme-linket immunosorbent assay plate was dried in air, 80 μl enzyme-labeled antibody was added to each well and incubated at 37° C. for 40 minutes. The plate was washed with wash solution for 4 times and dried in air, then 50 μl of substrate solution A and 50 μl of substrate solution B were added to each well and developed at 37° C. for 15 minutes under protection from light. Then 50 μl of stop solution was added to each well. $A_{450\ nm}$ values were detected on 550 type enzyme-linket immunosorbent assay detector. The median dilution times of the reference and the samples were calculated by program or linear regression method based on the median effect value of the reference of εPA44 (median maximum absorbance), and the potency of the test sample and the specific activity of the product were calculated according to the following formulas.

$$A = 2^{(na-ne)}$$

$$E = \frac{ma}{me};$$

$$SA = \frac{A}{C}$$

The detection results showed that the specific activity of the product was 13985.31 U/mg; and the potency of each vial was 4085.53 U.

70. Determining the Potency/Specific Activity of the Liposome of $CH_3(CH_2)_{14}$COKSSQYIKANSKFIGITEAAAFLPSDFFPSVGGGDPRVRGLYFPA (SEQ ID NO:1)

The liposome was washed, centrifuged, extracted and dried, and then dissolved and sampled to determine the content of εPA44 by RP-HPLC. The sample was diluted to a concentration measurable for the potency. The enzyme-linket immunosorbent assay plate was coated, blocked, bound by enzyme-labeled antibody, and developed. The absorbance at 450 nm (A450 nm) was detected at an enzyme-label device, and compared to the value of the reference of the product to determine the potency of the product in the extract of the sample and calculate the specific activity of the finished product.

The reference was diluted with 50% ethanol by ten folds, and then was serially diluted. 100 μl dilutions were separately added to 96-well enzyme-linket immunosorbent assay plate, each well was repeated in triplicate. Coating was carried out in refrigerator at 4° C. for 20-24 hours. The finished product was diluted and coated similarly to the reference. 100 μl of 50% ethanol was added to negative control wells. After the coating was completed, 200 μl of 1% calf serum was added to each well, and blocked in refrigerator at 4° C. for 2 hours. The enzyme-linket immunosorbent assay plate was dried in air, 80 μl of enzyme-labeled antibody was added to each well and incubated at 37° C. for 40 minutes. The enzyme-linket immunosorbent assay plate was washed with wash solution for 4 times and dried in air, then 50 μl of substrate solution A and 50 μl of substrate solution B were added to each well and developed at 37° C. for 15 minutes. 50 μl of stop buffer was added to each well. $A_{450\ nm}$ values were detected at a 550 type enzyme-linket immunosorbent assay detector. According to the median effect value of the reference of εPA44 (median maximum absorption), the median dilution factors of the reference and the samples were calculated by program or linear regression method. Then the potency of the test sample and the specific activity of the product were calculated according to the following formulas.

$$A = 2^{(na-ne)}$$
$$E = \frac{ma}{me};$$
$$SA = \frac{A}{C}$$

The detection results showed that the specific activity of the product was 14173.51 U/mg; and the potency of each vial was 4177.78 U.

---

What is claimed is:

1. An immunogen, with the structure $CH_3(CH_2)_{14}CO$-KSSOYIKANSKFIGITEAAAFLPSDFF-PSVGGGDPRVRGLYFPA (SEQ ID NO:1), wherein a modifying group, $CH_3(CH_2)_{14}CO-$, is covalently linked to the polypeptide sequence via the N-terminal epsilon-amino group.

2. A vaccine for treatment of hepatitis B, characterized in that said vaccine comprises an immunogen according to claim 1.

3. A vaccine for treatment of hepatitis B, characterized in that said vaccine comprises an immunogen according to claim 1 and pharmaceutically acceptable auxiliary materials, adjuvants and/or carriers.

4. A method for treatment of a chronic HBV persistent infection state and secondary diseases selected from the group consisting of liver cirrhosis and liver cancer, comprising administering an immunogen according to claim 1 to a subject in need thereof.

5. The method of claim 4, wherein the chronic HBV persistent infection state occurs in a patient with chronic hepatitis B or a carrier of hepatitis B virus.

6. A vaccine comprising an immunogen according to claim 1, wherein the vaccine is suitable for treatment of a chronic HBV persistent infection state and relevant secondary diseases selected from the group consisting of liver cirrhosis and liver cancer.

7. The vaccine of claim 6, wherein the chronic HBV persistent infection state occurs in a patient with chronic hepatitis B or a carrier of hepatitis B virus.

8. A vaccine for treatment of hepatitis B according to claim 6, characterized in that the formulation of said vaccine is injection formulation, percutaneous formulation, oral formulation, inhalant formulation or suppository formulation.

9. A vaccine for treatment of hepatitis B according to claim 6, characterized in that said vaccine is in liquid dosage form, suspension dosage form, liquid liposome dosage form or lyophilized liposome dosage form.

10. A vaccine for treatment of hepatitis B according to claim 9, characterized in that said liquid liposome dosage form or lyophilized liposome dosage form comprises phospholipids.

11. A vaccine for treatment of hepatitis B according to claim 10, characterized in that said liquid liposome dosage form or lyophilized liposome dosage form further comprises cholesterol.

12. A vaccine for treatment of hepatitis B according to claim 10, characterized in that said liquid liposome dosage form or lyophilized liposome dosage form further comprises vitamin E.

13. A vaccine for treatment of hepatitis B according to claim 10, characterized in that said liquid liposome dosage form or lyophilized liposome dosage form further comprises palmitic acid.

14. A vaccine for treatment of hepatitis B according to claim 9, characterized in that said lyophilized liposome dosage form further comprises human albumin, mannitol and phosphates.

15. A vaccine for treatment of hepatitis B according to claim 9, characterized in that said lyophilized liposome dosage form comprises an immunogen according to claim 1, phospholipids, cholesterol, palmitic acid, vitamin E, mannitol, human albumin, $KH_2PO_4$ and $Na_2PO_4$ in a molar ratio of 0.01-0.1:5-15:1-7:0.5-1.5:0.5-1.5:70-150:0.1-0.3:1-10:1-10.

16. An immunogen comprising a Th-cell epitope consisting of the amino acid sequence QYIKANSKFIGITE (SEQ ID NO:6) linked to a CTL epitope consisting of the amino acid sequence FLPSDFFPSV (SEQ ID NO:23) linked to a B-cell epitope consisting of the amino acid sequence DPRVIRGLYFPA (SEQ ID NO:48), wherein:

a modifying group $CH_3(CH_2)_{14}CO-$ is covalently linked to an N-terminal epsilon-amino group on a linking peptide KSS; and the Th-cell epitope, CTL epitope, and B-cell epitope are covalently linked together by linking peptides consisting of 3-7 amino acid residues.

* * * * *

UNITED STATES PATENT AND TRADEMARK OFFICE
CERTIFICATE OF CORRECTION

PATENT NO. : 8,591,908 B2  
APPLICATION NO. : 10/528350  
DATED : November 26, 2013  
INVENTOR(S) : Y. Wu et al.

Page 1 of 1

It is certified that error appears in the above-identified patent and that said Letters Patent is hereby corrected as shown below:

In the Claims

| COLUMN | LINE | ERROR |
|---|---|---|
| 75 (Claim 1, | 36-37 line 2) | "$CH_3(CH_2)_{14}CO$-KSSOYIKANSKFIGITEAAAFLPSDFFPSVGGGDPRVRGLYFPA" should read<br><br>--$CH_3(CH_2)_{14}CO$-KSSQYIKANSKFIGITEAAAFLPSDFFPSVGGGDPRVRGLYFPA-- |

Signed and Sealed this  
Twenty-second Day of April, 2014

Michelle K. Lee  
*Deputy Director of the United States Patent and Trademark Office*